(12) United States Patent
Kauppinen

(10) Patent No.: US 7,797,983 B2
(45) Date of Patent: Sep. 21, 2010

(54) METHOD AND SYSTEM FOR DETECTING ONE OR MORE GASES OR GAS MIXTURES AND/OR FOR MEASURING THE CONCENTRATION OF ONE OR MORE GASES OR GAS MIXTURES

(75) Inventor: Jyrki Kauppinen, Ilmarinen (FI)

(73) Assignee: Gasera Ltd., Turku (FI)

( * ) Notice: Subject to any disclaimer, the term of this patent is extended or adjusted under 35 U.S.C. 154(b) by 648 days.

(21) Appl. No.: 11/547,084

(22) PCT Filed: Mar. 29, 2004

(86) PCT No.: PCT/FI2004/000180

§ 371 (c)(1),
(2), (4) Date: Sep. 29, 2006

(87) PCT Pub. No.: WO2005/093390

PCT Pub. Date: Oct. 6, 2005

(65) Prior Publication Data

US 2007/0151325 A1    Jul. 5, 2007

(51) Int. Cl.
    *G01N 21/84*    (2006.01)
(52) U.S. Cl. .................. 73/24.02; 73/24.06; 250/339.13
(58) Field of Classification Search ............ 73/24.01, 73/24.02, 24.06; 250/339.13
    See application file for complete search history.

(56) References Cited

U.S. PATENT DOCUMENTS

| | | | |
|---|---|---|---|
| 2,924,713 A | 2/1960 | Liston | |
| 3,937,962 A * | 2/1976 | Faulhaber et al. | 250/346 |
| 4,055,764 A | 10/1977 | Dimeff | |
| 4,236,827 A | 12/1980 | Horiba et al. | |
| 4,373,137 A | 2/1983 | Fabinski et al. | |
| 4,594,004 A * | 6/1986 | Ishida et al. | 356/433 |
| 4,682,031 A | 7/1987 | Fabinski et al. | |
| 4,817,413 A * | 4/1989 | Asano et al. | 73/24.02 |
| 5,055,688 A | 10/1991 | Fabinski | |

(Continued)

FOREIGN PATENT DOCUMENTS

EP    1 191 812 A1    3/2002

(Continued)

OTHER PUBLICATIONS

Kauppinen, J. et al. "High Sensitivity in Gas Analysis with Photoacoustic Detection", Microchemical Journal, vol. 76, Issues 1-2, Feb. 2004, pp. 151-159.*

(Continued)

*Primary Examiner*—Daniel S Larkin
(74) *Attorney, Agent, or Firm*—Buchanan Ingersoll & Rooney PC

(57) ABSTRACT

The invention relates to a system and method for detecting one or more gases or gas mixtures and/or for measuring the concentration of one or more gases or gas mixtures, said system comprising at least a light source, a sample space, a reference chamber, and a measuring chamber. The measuring chamber is supplied with a gas to be detected or measured. In addition, the measuring chamber is provided with a pressure sensor for detecting a photoacoustic signal generated in the measuring chamber. The pressure sensor comprises either a door, whose movement is measured without contact, or a sensor, whose movement is measured optically.

14 Claims, 16 Drawing Sheets

U.S. PATENT DOCUMENTS

Figure 1:
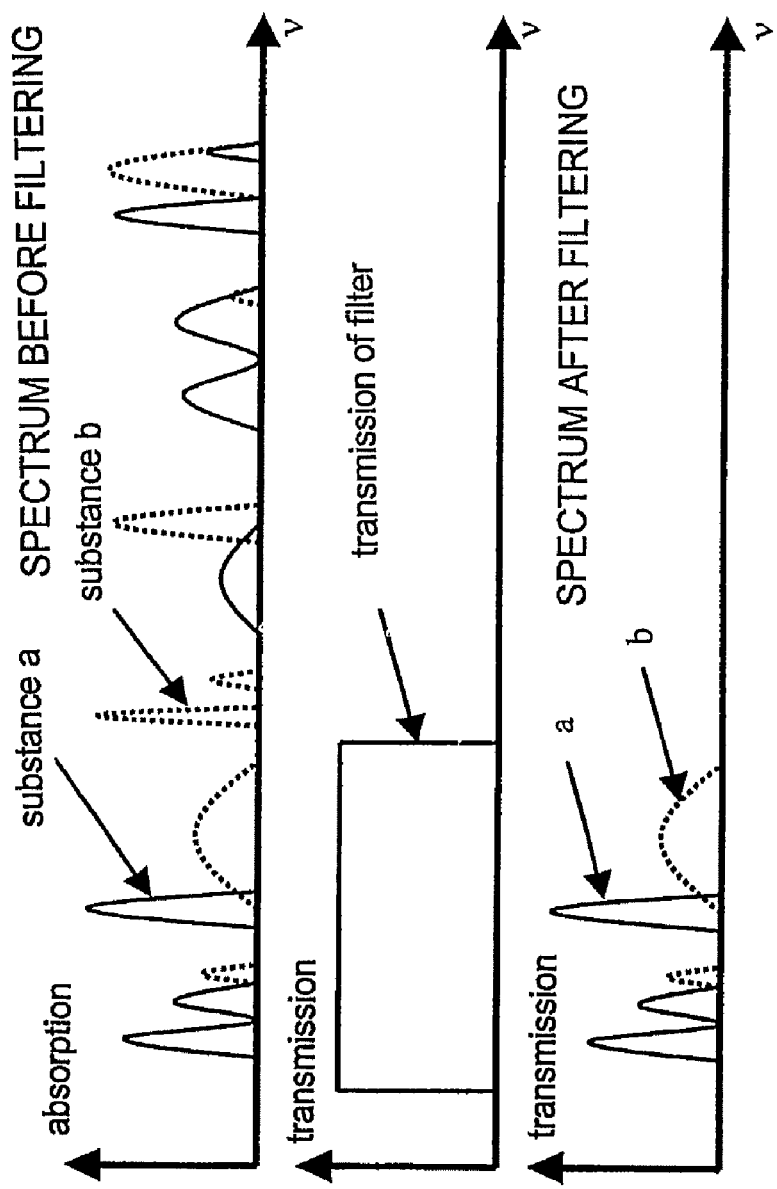

| | | | |
|---|---|---|---|
| 5,537,854 A * | 7/1996 | Phillips et al. | 73/24.01 |
| 5,581,014 A * | 12/1996 | Douglas | 73/24.01 |
| 6,452,182 B1 | 9/2002 | Zochbauer et al. | |
| 6,694,031 B2 | 2/2004 | Paritsky et al. | |
| 7,091,869 B2 * | 8/2006 | Forster et al. | 340/628 |

FOREIGN PATENT DOCUMENTS

| | | |
|---|---|---|
| WO | 99/44040 | 9/1999 |
| WO | 2004/029593 A1 | 4/2004 |
| WO | 2004/029594 A1 | 4/2004 |

OTHER PUBLICATIONS

A.A. Kovalyov et al., "Resonant optoacoustic detector in nondispersive gas analyzer scheme", Infrared Physics & Technology 38, 1977, pp. 415-421.

Frans J.M. Harren, et al., "Photoacoustic Spectroscopy in Trace Gas Monitoring", Encyclopedia of Analytical Chemistry, John Wiley & Sons Ltd, Chichester, 2000, pp. 2203-2226.

* cited by examiner

METHOD AND SYSTEM FOR DETECTING ONE OR MORE GASES OR GAS MIXTURES AND/OR FOR MEASURING THE CONCENTRATION OF ONE OR MORE GASES OR GAS MIXTURES

BACKGROUND

The invention relates to a method and a system as set forth in the preambles of the appended independent claims for detecting one or more gases or gas mixtures and/or for measuring the concentration of one or more gases or gas mixtures.

Typically, the detection of various gases and gas mixtures, as well as concentrations thereof, is performed by using detectors based on photoacoustic phenomenon. When light falls in a gas-filled chamber, which contains a gas to be analysed at a partial pressure px and a carrier gas at a partial pressure pN (typically often nitrogen), radiation is absorbed by the gas px. The purpose is to measure the partial pressure px of a gas x. After the absorption process, energy converts to a thermal motion at a certain time constant τ (e.g. $10^{-5}$ s). Thus, the entire gas has its temperature rising by ΔT per unit time. The temperature rise also brings about a pressure rise Δp, which can be converted to a photoacoustic signal or which can be used as a photoacoustic signal. The term light used in this application should be perceived in a general sense, as in reference to electromagnetic radiation, comprising e.g. ultraviolet radiation, visible light, infrared radiation, and microwaves. Respectively, the term light beam covers electromagnetic beams in general, and the term light source encompasses generally various sources of electromagnetic radiation.

A typical photoacoustic detector comprises a chamber, which can be supplied with a gas or gas mixture to be analysed, a window for admitting modulated or pulsed infrared radiation or light into the chamber, and a pressure sensor arranged to measure pressure variations in the chamber generated by absorbed infrared radiation or light. The pressure sensor is typically a microphone, in which the movement of a thin Mylar or metal diaphragm is measured, for example capacitively. A photoacoustic detector can be used for measuring or detecting infrared radiation generally, but one specific and important application of such a detector involves measuring or detecting gases or gas mixtures, for example in relation to the quality or pollutions of air.

Typically, a photoacoustic detector is connected to a spectrometer, whereby the spectrometer can be used for detecting various gases in a gas mixture and/or for measuring the concentrations or partial pressures of gases. If a photoacoustic detector is to be used for measurements without a spectrometer, the detector must be selective for a gas to be examined. According to prior known techniques, the selectivity in a photoacoustic process is typically achieved by using a laser as its radiation source, which has its wavelength coinciding with the wavelength of any absorption line of the gas. Another prior known option is to employ an optical filter in connection with a broadband emitter, whereby a desired wavelength range is established by selecting an optical filter having desired filtering properties.

A problem in laser-based measurement is typically its laborious use. Another problem with lasers is the limited range of available wavelengths, thereby limiting the range of substances that can be analysed.

A problem with an optical filter is typically poor quality filtration, the optical filter not being optimal in terms of its selectivity. FIG. 1 illustrates the operation of an optical filter. If there are several gas absorptions within a filter area, the signals thereof are summed and the result will be a sum of the concentrations of the gases. A photoacoustic signal represents the area of a spectrum transmitted through the filter. The signal is weak because a signal is generated only by a fraction of the spectrum of a substance being analysed.

Kovalyov and Klebleyev (A. A. Kovalyov, N. R. Klebleyev, *Resonant optoacoustic detector in nondispersive gas analyzer scheme*, Infrared Physics & Technology 38, 1997, pp. 415-421) have proposed the replacement of an optical filter with a chamber, containing a gas to be measured at a known pressure p0x. According to what is set forth in this publication, the measuring chamber of a photoacoustic detector is supplied with a sample of gas to be analysed, the objective being to measure the analysable gas mixture contained therein for a partial pressure px of its gas x. The chamber is supplied with a pulsed light beam, the first of which is passed, prior to the measuring chamber, through a void reference space and the second of which is passed, prior to the measuring chamber, through a filter chamber containing the gas x to be analysed at a known pressure p0x. The photoacoustic detector, and especially its measuring chamber, has been arranged in such a configuration that, if the gas sample supplied into the measuring chamber does not contain a gas identical to the gas presently in the filter chamber, the chamber shall not develop a pressure variation detected by a microphone in the measuring chamber. If the gas sample arranged into the measuring chamber does contain a gas identical to that in the filter chamber, a photoacoustic pressure variation, i.e. a photoacoustic signal, will be detected by the microphone.

The most notable problem in the solution proposed by Kovalyov and Klebleyev is its insensitivity, which is at best equal to that of a conventional method comprising only a photoacoustic measuring chamber. The reason for this is that, unlike an optical filter, a filter chamber is not capable of providing a 100% absorption. If the absorption of a filter chamber is increased by means of pressure to the proximity of 100%, the breadths of absorption lines shall increase, thus impairing the method as regards its selectivity. In addition, the pressure sensor employed is a capacitive microphone, wherein sensitivity is limited by a stiffness of the diaphragm and a capacitive measurement of the diaphragm motion. In a capacitive microphone, some of the energy of diaphragm motion is spent for the alternating flow of gas in and out between diaphragm and electrode.

Publication U.S. Pat. No. 4,373,137 also discloses a method for measuring a photoacoustic pressure signal generated in a two-section measuring chamber by a pulsed light beam passing through a sample chamber. The pressure difference between successive measuring chambers is measured capacitively by means of a diaphragm, which results in a poor sensitivity of the method as described above.

In addition, patent publications U.S. Pat. No. 5,055,688 and U.S. Pat. No. 4,682,031 describe measuring systems, including a measuring device which comprises sample and reference chambers set side by side for conducting modulated light beams therethrough into a measuring chamber. A problem with the solutions disclosed in these publications is also that the pressure sensors used therein are not sufficiently sensitive, being based on a capacitive measurement of the diaphragm motion.

Patent publication U.S. Pat. No. 6,452,182 further discloses a photometer, comprising a plurality of successively arranged measuring chambers, containing an isotope of the gas to be examined which is different from the one in the preceding chambers. The described solution is typically aimed at enabling a measurement of various isotopes of a gas with a single device in a single measurement. However, a problem with the measuring systems disclosed in the publication is the insensitivity thereof, for the reason mentioned above.

Another problem in prior known photoacoustic detectors is the sensitivity thereof to external sounds. Therefore, the gas space in prior known photoacoustic detectors must be sealed, i.e. it is not possible to use an open gas space but, instead, the gas space functioning as a sample space must be separately filled with a sample to be measured, typically gas.

SUMMARY

It is indeed an object for a method and system of the present invention to eliminate or at least to alleviate problems arising from the prior art as described above.

A further object for a method and system of the present invention is to provide a selective and sensitive photoacoustic detector with no need for an optical filter.

A still further object of the present invention is to provide a method and a system, capable of suppressing the effect on a measuring result caused by disturbing factors due to external sounds.

In order to accomplish the above objects, among others, a method and system of the invention are principally characterized by what is set forth in the characterizing clauses of the appended independent claims.

Accordingly, the invention relates typically to a system for detecting one or more gases or gas mixtures and/or for measuring the concentration of one or more gases or gas mixtures, said system comprising at least a first light source, and a sample space to which gas to be detected and/or measured can be arranged, as well as a reference space isolated from the sample space and containing no gas to be detected and/or measured. In addition, a typical system of the present invention comprises a measuring chamber, having a volume V, and to which measuring chamber gas or gas mixture to be detected and/or measured has been arranged. At least one aperture has been typically arranged in a wall of the measuring chamber, said aperture being provided with a window for admitting modulated and/or pulsed infrared radiation and/or light into the measuring chamber. Furthermore, a typical system comprises means for conducting a first light beam from the first light source into the sample space and further into the measuring chamber, as well as means for conducting a second light beam, in isolation from the sample space, from the first light source or a possible second light source into the reference space and further into the measuring chamber. Additionally, a typical system comprises means for pulsing the first and second light beams.

A measuring chamber according to one embodiment of the invention comprises two chambers in communication with each other by way of an aperture, the first being supplied with said first light beam and the second with said second light beam, and that a door arranged to move in response to a pressure difference between the first and second measuring chambers has been arranged in the aperture, and that the measuring chamber comprises means for measuring the door movement without contact.

In a system according to another embodiment of the present invention, the measuring chamber comprises means for detecting pressure variations produced in the measuring chamber by absorbed infrared radiation and/or light, said means comprising at least an aperture arranged in a wall of the measuring chamber, in connection to which aperture a door arranged to move in response to a gas pressure has been arranged, and means for measuring the door movement without contact.

In this context, measuring the door movement without contact is in reference to measuring procedures, which are performed without one or more sensors mounted on the door or in mechanical engagement or contact therewith, such as, for example, without a piezoelectric sensor mounted on the door surface. Thus, in such non-contact measurement, the door does not have mounted thereon or connected therewith any such measuring equipment which would disturb and/or buff the door movement. Such non-contact measuring methods include, for example, various optical measuring techniques. Another measuring method considered as non-contact is the above-described capacitive measurement, in which one of the capacitor plates is adapted to comprise a door of the present invention.

In this context, the sample space refers to a defined or undefined, isolated or non-isolated, sealable or open space, which can be supplied with gas or gas mixture to be detected and/or measured or into which it is able to migrate freely or in a controlled manner and through which space it is possible to provide a light beam. Hence, such a sample space may be for example a closed and environment-proof chamber, which has at least one fitting, such as for example a faucet or a valve, for filling and draining the chamber with a desired gas or gas mixture. The sample space can also be for example a tubular space where have been arranged holes for providing for the gas a free or controlled admission into the sample space. The sample space may also be an imaginary and almost unlimited space, which develops along the path of a light beam to be conducted into the space. Supplying gas into the sample space refers to all procedures, by virtue of which the sample space shall contain gas or gas mixture to be detected/measured. Such procedures include for example delivery of gas into a sample space or bringing of an at least partially open sample space to a location or a facility containing gas or gas mixture to be detected/measured. The sample space can also be for example a process tube or container for flowing and/or storage of gas, gas mixture, liquid, or solid substance used in a process, such as a pharmaceutical production process. The sample space can also be for example a tube or pipe, containing flue gases of a combustion process, or an anticipated extension thereof.

The reference space refers in this context to a defined space isolated from the sample space, which does not contain gas mixture or gas to be detected and/or measured or it is present in a known amount. The reference space may contain for example some suitable gas non-absorbing in a desired wavelength range, such as for example nitrogen in infrared range.

In this context, the first and second light beam does not refer to the temporal and time-linked order of light beams, but the terms first and second are only used for distinguishing the light beams from each other. Hence, it is possible that, in temporal sequence, the first light beam be conducted into either one of the sample space or the reference space.

Pulsing of a light beam refers in this context to the sequencing of light beams in such a way that the light beams are allowed to travel in known temporal cycles through the sample space or the reference space into a measuring chamber. Pulsing can be implemented synchronously or asynchronously. In synchronous pulsing, the first and second light beams are allowed to travel concurrently through sample and reference spaces. In asynchronous pulsing, the light beams are allowed to travel alternately either through a sample space or a reference space. In some applications, the asynchronous pulsing can also be implemented in such a manner that the light beams are allowed to travel some of the time concurrently through sample and reference spaces and some of the time alternately through either one of the spaces. Pulsing can be effected either electrically or mechanically. Thus, pulsing can be implemented for example by using separate light sources for first and second light beams and by switching said light sources on and off at a desired rate. For example, pulsing of a laser can be performed by controlling a supply current to the laser. Pulsing can also be effected by using a mechanical chopper, which is capable of pulsing light beams supplied from one and the same light source into sample and reference spaces.

In one system of the present invention, the door has a surface area which is not larger than equal to that of an aperture arranged in the chamber. The aperture area represents in this context the surface area of an imaginary plane surface in the aperture. The door surface area represents the surface area of the azimuthal projection of a door projected onto the imaginary plane surface of the aperture. Accordingly, if the door has, for example, a curvilinear surface, it is possible that the door has an actual surface area which is larger than that of the aperture, but even in this case, the azimuthal projection of a door of the present invention has a surface area which is smaller than that of the aperture.

In one system of the present invention, the door is fastened at least along one side to a frame structure encircling the lateral door surfaces. In a highly preferred case, the door and the frame are constructed in silicon, for example by forming a slot in a silicon disc, which, aside from the fastening points, separates the door from the other section of the disc that forms the frame.

In one system of the present invention, the means for measuring a door movement without contact comprise: an optical measuring assembly, comprising at least one or more light sources for lighting a door or a section thereof and one or more detectors for receiving the light reflected from the door and for measuring the door movement as an optical angular and/or translatory measurement, or a capacitive measuring assembly, wherein a door or a section thereof is plated with metal or a door is manufactured in an electrically highly conductive material, and said measuring assembly comprising a metal diaphragm or a metal-plated diaphragm, arranged in the proximity of the door, as well as means for measuring changes in the capacitance of a capacitor constituted by the door and the metal diaphragm. In some applications, the system may also comprise both optical and capacitive measuring assemblies. It is also possible that, in addition to an optical and/or capacitive measuring assembly, the system comprises also other measuring assemblies for measuring the door movement without contact.

According to one embodiment of the present invention, the measuring chamber comprises two chambers in communication with each other by way of an aperture, the first being supplied with said first light beam and the second with said second light beam. The aperture is provided with a sensor adapted to move in response to gas pressure variation taking place in the first and/or second section of the measuring chamber. In addition, means are provided in the measuring chamber or in communication therewith for measuring the sensor movement optically.

In one system of the present invention, the measuring chamber comprises at least one aperture, whereby the measuring chamber is exhaustible and through which the measuring chamber at least one gas to be detected and/or measured at a known partial pressure can be arranged.

In addition, a system according to one embodiment of the invention comprises means for subtracting a first photoacoustic signal from a photoacoustic signal generated by the second light beam. A system according to one embodiment of the invention comprises a phase locked loop for measuring the amplitude of a photoacoustic signal.

In one system of the present invention, the measuring chamber is arranged as a Helmholtz resonator.

In one system of the present invention, the first and second light beams are arranged to be generated with one and the same light source.

In one system of the present invention, the first and second light beams are arranged to be generated with separate light sources.

In one system of the present invention, the sample space is arranged to be at least partially open to the environment, whereby gas to be detected and/or measured can freely pass into the sample space. According to one embodiment of the invention, the sample space comprises a tubular space, which is provided with holes for a free or controlled passage of gas into the sample space. According to one embodiment of the invention, the sample space is an imaginary and almost unlimited space, which develops along the path of a light beam conducted into the space. An advantage gained by such a sample space, into which gas to be detected and/or measured is able to find a free passage, is that there is no need for special arrangements for passing gas to be detected and/or measured into the sample space, as it is sufficient to take the sample space to a location, which contains or is expected to contain gas to be detected and/or measured. A system, provided with such a totally or partially open sample space, can be used for example in measuring equipment or alarm devices, which are used for analysing respiratory or indoor air or gas evaporating from liquid or solid matter.

According to one embodiment of the invention, the sample space is a process tube or container, which is used for flowing and/or storing some gas, gas mixture, liquid, or solid substance used in a process, such as a pharmaceutical production process. Thus, a system and method of the present invention can be utilized in measurements and monitoring involved in the discussed process and its management, control, and/or supervision.

According to one embodiment of the invention, the sample space is a tube or pipe containing flue gases of a combustion process, or an anticipated extension thereof. Thus, a system and method of the present invention can be used for the management, control, and/or supervision of a combustion process or, for example, for monitoring and measuring discharges.

In one system of the present invention, gas or gas mixture, which neither contains gas to be measured or detected nor causes absorption of a light beam in a desired wavelength range is arranged to the reference space. One notable example of a gas like this is nitrogen.

In one system of the present invention, the system comprises measuring chambers, isolated from each other, containing various gases, and including a sensor adapted to move in response to gas pressure variation, and means for shifting the measuring chambers alternately to receive a first and second light beam for effecting a measurement.

In one system of the present invention, the system comprises several measuring chambers, isolated from each other, containing various gases, and including a sensor adapted to move in response to gas pressure variation, said measuring chambers being arranged such that the first and second light beams travel through all measuring chambers without shifting a measuring chamber.

In one system of the present invention, the measuring chambers are arranged in succession.

In one system of the present invention, the measuring chambers are arranged side by side, and that said system comprises means for splitting the first and second light beams into equal beams and for guiding the same into the measuring chambers.

A method according to one embodiment of the invention for detecting one or more gases or gas mixtures or for measuring the concentration of one or more gases or gas mixtures comprises at least the following steps of:

conducting a first light beam into a sample space to which gas to be detected and/or gas mixture to be measured is arranged for measuring a desired component x thereof for its partial pressure px, and further into a measuring chamber isolated from the sample space, to which measuring chamber gas, which is to be detected and/or measured and which is at a known pressure p0x is arranged, and said measuring chamber comprises two chambers in communication with each other by way of an aperture, the first one being supplied with said first light beam, and to which aperture between the chambers, a door arranged to move in response to a pressure difference between the first and second measuring chambers has been arranged, conducting a second light beam into a reference space isolated from the sample space and further into a measuring chamber isolated from the reference space, such that the second light beam, at least upstream of the measuring chamber, is always isolated from the sample space and arrives in a section of the measuring chamber other than the one receiving the first light beam, pulsing the first and second light beams, such that a photoacoustic signal is produced thereby for a photoacoustic pressure sensor arranged in the measuring chamber, and detecting the photoacoustic signal by measuring said door movement without contact, said signal being used for detecting the gas x and/or for measuring the concentration or the partial pressure px of a gas from a gas mixture.

A method according to one embodiment of the invention for detecting one or more gases or gas mixtures or for measuring the concentration of one or more gases or gas mixtures comprises at least the following steps of:

conducting a first light beam into a sample space to which gas to be detected and/or gas mixture to be measured has been arranged for measuring a desired component x thereof for its partial pressure px, and further into a measuring chamber isolated from the sample space, to which measuring chamber gas, which is to be detected and/or measured and which is at a known pressure p0x has been arranged, and said measuring chamber comprising two chambers in communication with each other by way of an aperture, the first one being supplied with said first light beam, and to which aperture between the chambers a sensor arranged to move in response to a pressure difference between the first and second measuring chambers is arranged, conducting a second light beam into a reference space isolated from the sample space and further into a measuring chamber isolated from the reference space, such that the second light beam, at least upstream of the measuring chamber, is always isolated from the sample space and arrives in a section of the measuring chamber other than the one receiving the first light beam, pulsing the first and second light beams, such that a photoacoustic signal is produced thereby for a photoacoustic pressure sensor fitted in the measuring chamber, and detecting the photoacoustic signal by measuring said sensor movement optically, said signal being used for detecting the gas x and/or for measuring the concentration or the partial pressure px of a gas from a gas mixture.

A method according to one embodiment of the invention for detecting one or more gases or gas mixtures or for measuring the concentration of one or more gases or gas mixtures, said method comprising at least the following steps of:

conducting a first light beam into a sample space to which gas to be detected and/or gas mixture to be measured has been arranged for measuring a desired component x thereof for its partial pressure px, and further into a measuring chamber isolated from the sample space, to which measuring chamber gas, which is to be detected and/or measured and which is at a known pressure p0x is arranged, and said measuring chamber having a volume V and to a wall of which measuring chamber at least one aperture is arranged, being provided with a window for admitting a first light beam into the measuring chamber, and said measuring chamber comprising means for detecting pressure variations produced in the measuring chamber by absorbed infrared radiation and/or light, said means comprising at least an aperture arranged in a wall of the measuring chamber, in connection to which aperture a door arranged to move in response to a gas pressure variation is arranged, and means for measuring the door movement without contact conducting a second light beam into a reference space isolated from the sample space and further into a measuring chamber isolated from the reference space, such that the second light beam, at least upstream of the measuring chamber, is always isolated from the sample space and arrives in the measuring chamber through said window or a separate second window arranged to the measuring chamber, pulsing the first and second light beams, such that a photoacoustic signal is produced thereby for a photoacoustic pressure sensor arranged in the measuring chamber, and detecting the photoacoustic signal by measuring with the above-identified means, and using the detected photoacoustic signal for detecting the gas x and/or for measuring the concentration or the partial pressure px of a gas from a gas mixture.

In some applications, the measuring chamber only contains the gas x to be measured. In some embodiments, it is possible for the measuring chamber to contain some other gas as well, preferably in a known amount.

In one method of the present invention, the measuring chamber is exhausted prior to measuring, followed by supplying it with a gas x to be detected and/or measured at a known pressure p0x. This makes it possible to switch a gas or gases present in the measuring chamber, whereby one and the same photoacoustic detector can be used for measuring several different substances.

In one method of the present invention, the first and second light beams are produced by a single light source. An advantage gained by using a single light source is that the first and second light beams will be definitely equal in terms of strength.

In one method of the present invention, the first and second light beams are produced by separate light sources. An advantage gained by separate light sources is that, in some applications, the detector will be simpler in terms of its mechanical construction as no separate chopper is needed for pulsing. The choice between using one light source or two light sources must be made as required by a particular application. Accordingly, if a structurally simple solution is required for example in a particular application, the choice is to use two separate light sources. Respectively, when it is particularly important for an application to have a measurement which is as accurate and reliable as possible, the choice is to use a single light source.

In one method of the present invention, the method is applied for a concurrent detection of several gases, the measuring chamber being supplied with a mixture of gases subject to detection, and the detection threshold for one or more gases being determined by adjusting known partial pressures of the gases.

In one method of the present invention, the method is applied for a concurrent detection of several gases, the various gases being measured temporally in succession by providing for each gas to be measured a measuring chamber, which is isolated from other chambers and which comprises a photoacoustic pressure sensor and to which gas to be measured is arranged, and wherein the measuring chambers are arranged to receive the first and second light beams for effecting a measurement temporally in succession.

In one method of the present invention, the method is applied for a concurrent detection of several gases, the various gases being measured simultaneously by providing for each gas to be measured a measuring chamber, which is isolated from other chambers and which comprises a photoacoustic pressure sensor and to which gas to be measured is arranged, and by setting the measuring chambers in such a configuration that the first light beam and the second light beam travel through the measuring chambers.

In one method of the present invention, at least some of the measuring chambers are arranged one after the other. By supplying different gases or gas mixtures into the measuring chamber arranged one after the other, and by arranging the path of the first and second beams through these successive chambers, it is enabled to measure and/or detect several different gases by a single measurement system, typically at one measurement.

In one method of the present invention, at least some of the measuring chambers are arranged side by side, the first light beam and the second light beam being split for equal beams which are guided into the measuring chambers. This is another solution which enables measuring and/or detecting several different gases by a single measurement.

In one method of the present invention, the employed measuring chamber uses a Helmholtz resonator, which increases a pressure pulse at resonance frequency.

BRIEF DESCRIPTION OF THE DRAWING FIGURES

Figure 2:
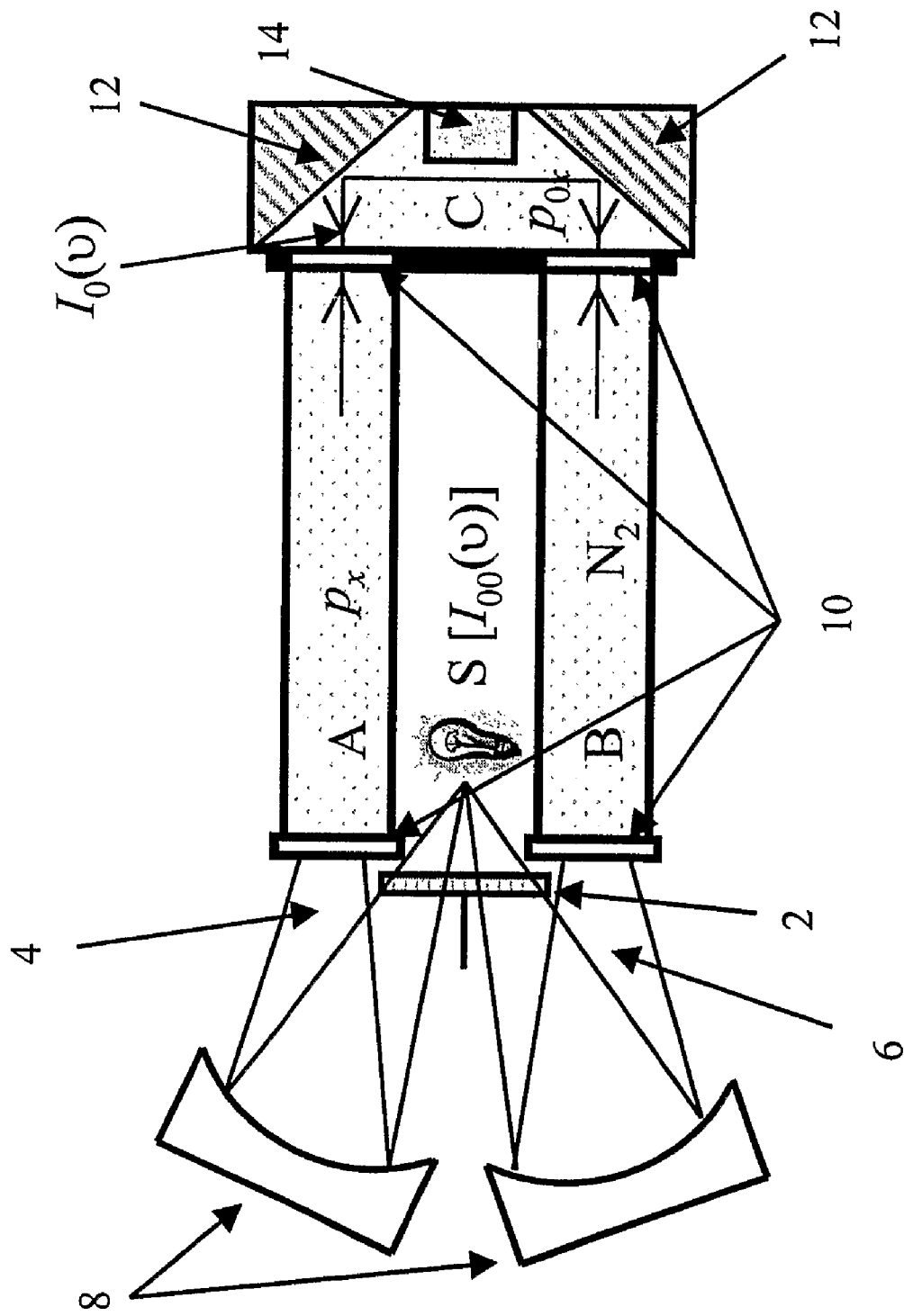
Figure 3:
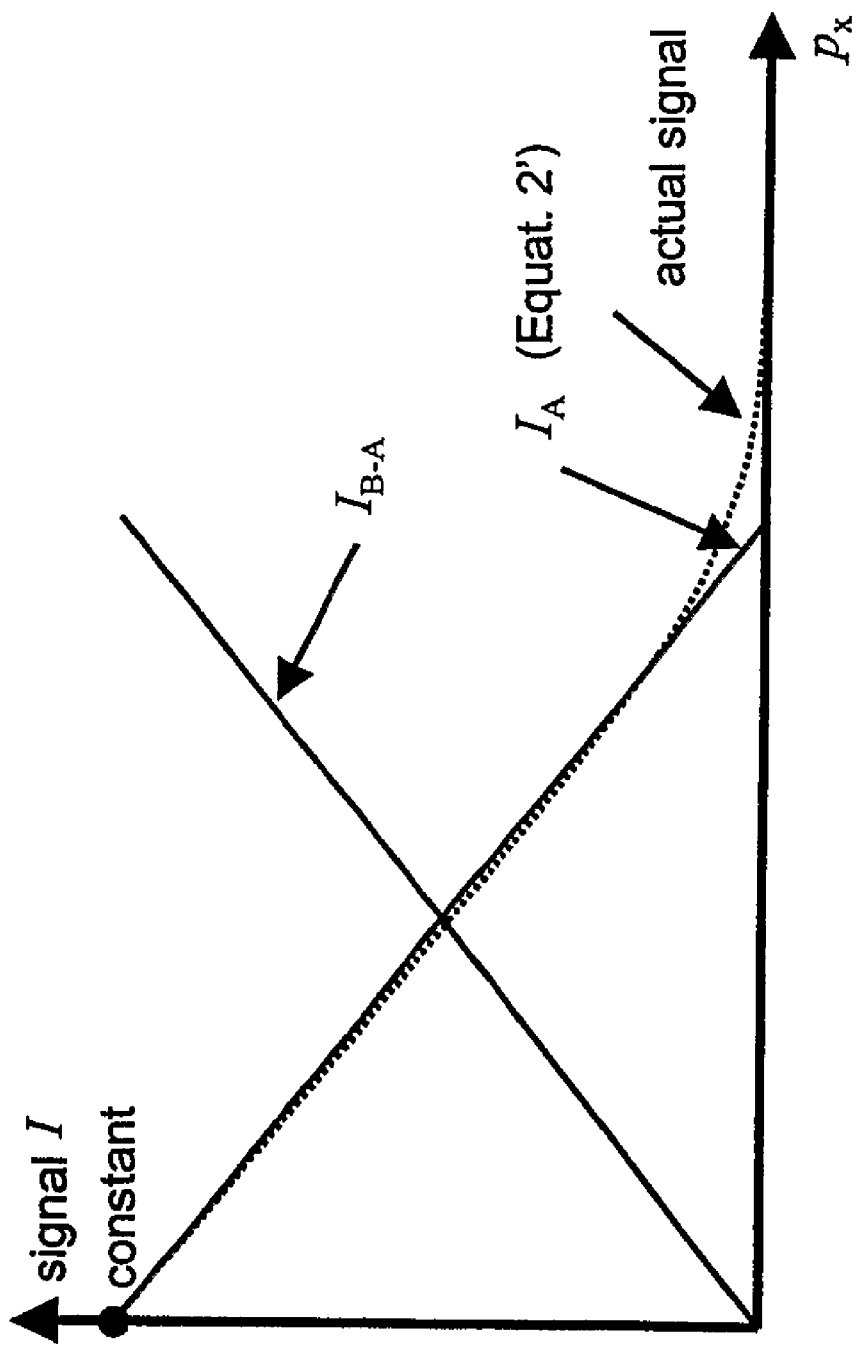
Figure 4:
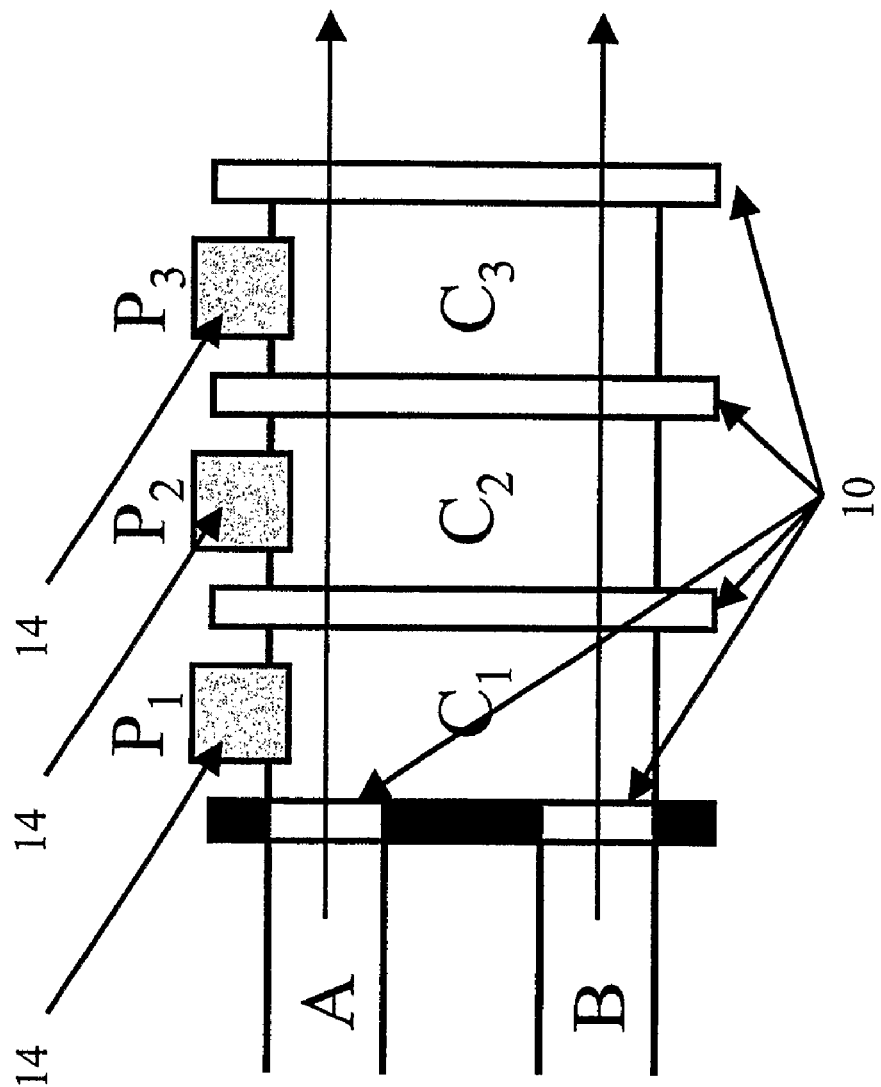
Figure 5:
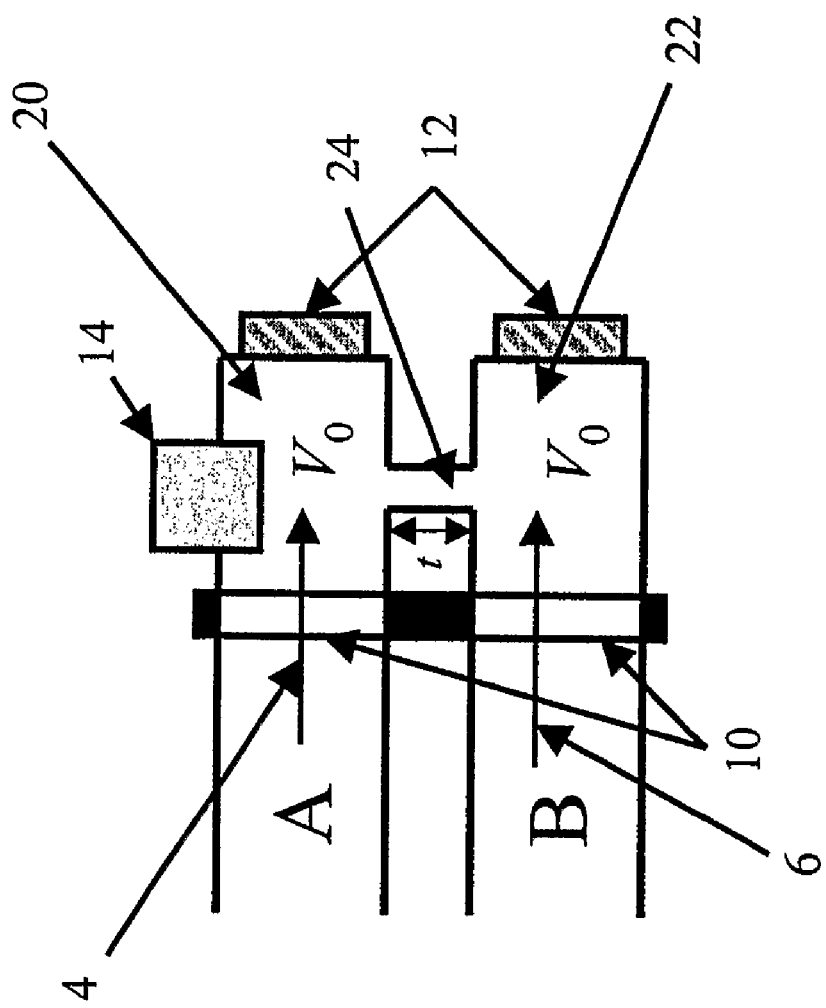
Figure 6:
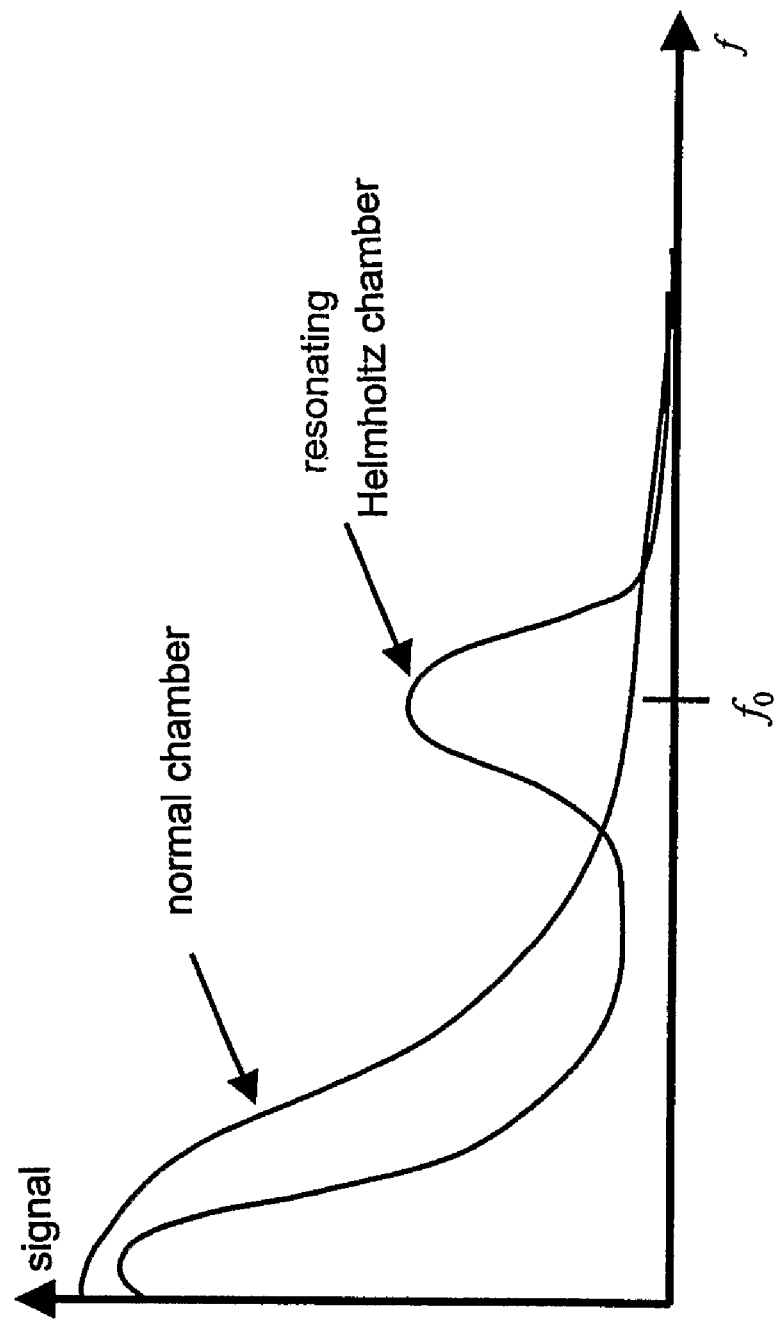
Figure 7:
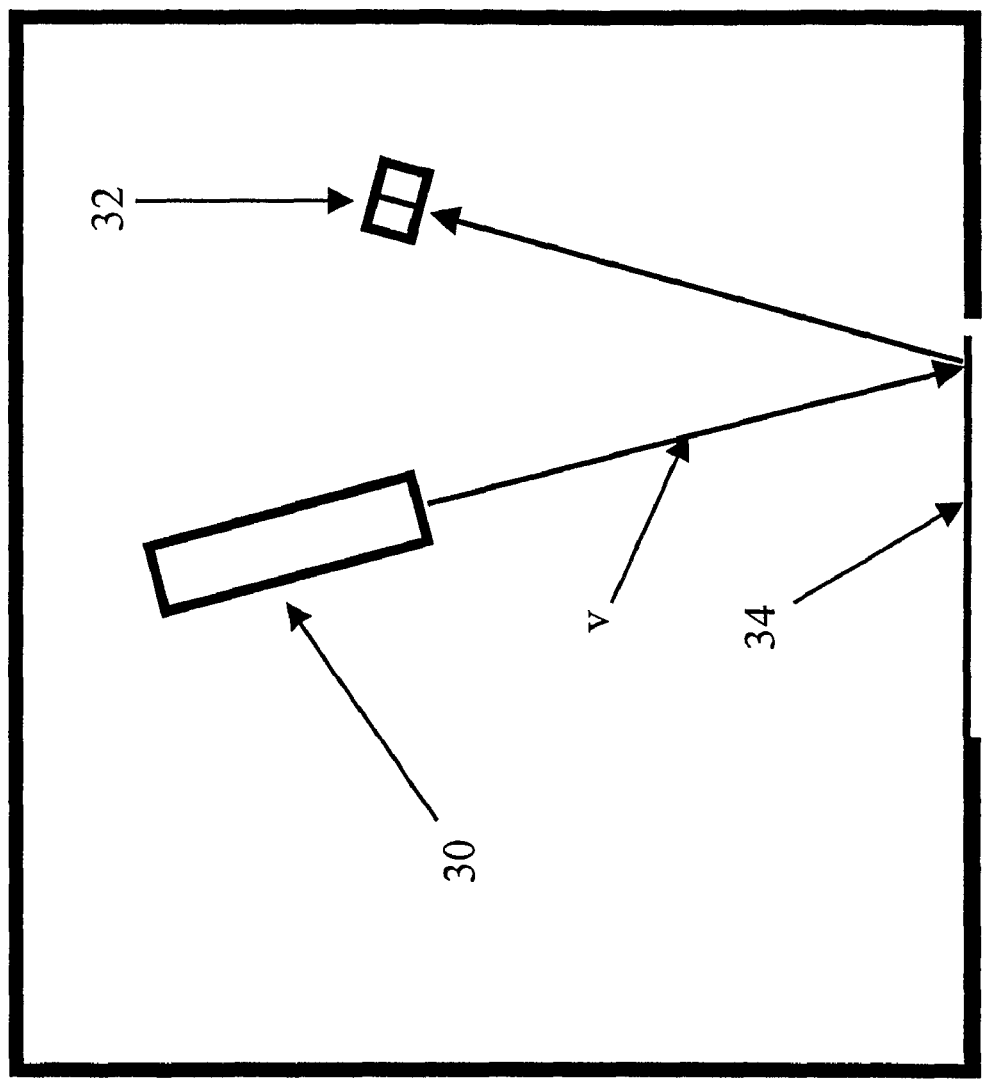
Figure 8:
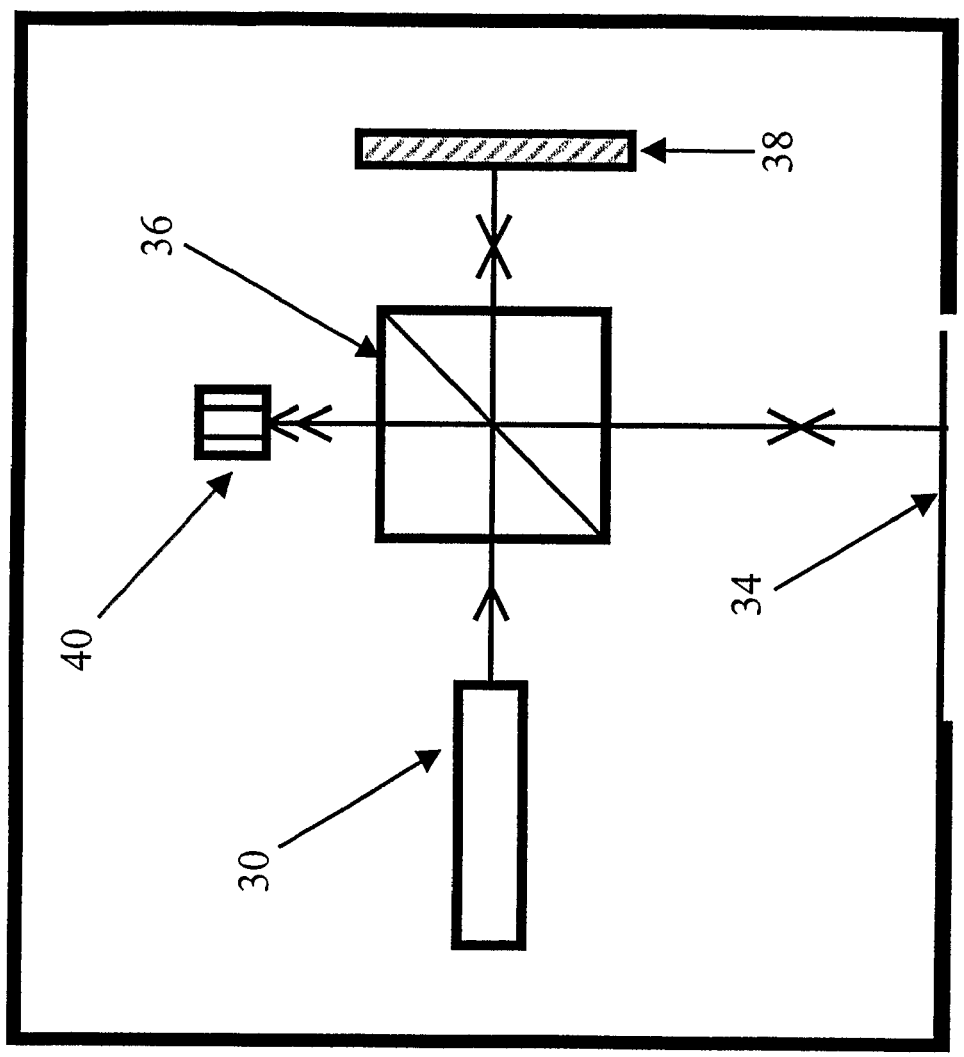
Figure 9A:
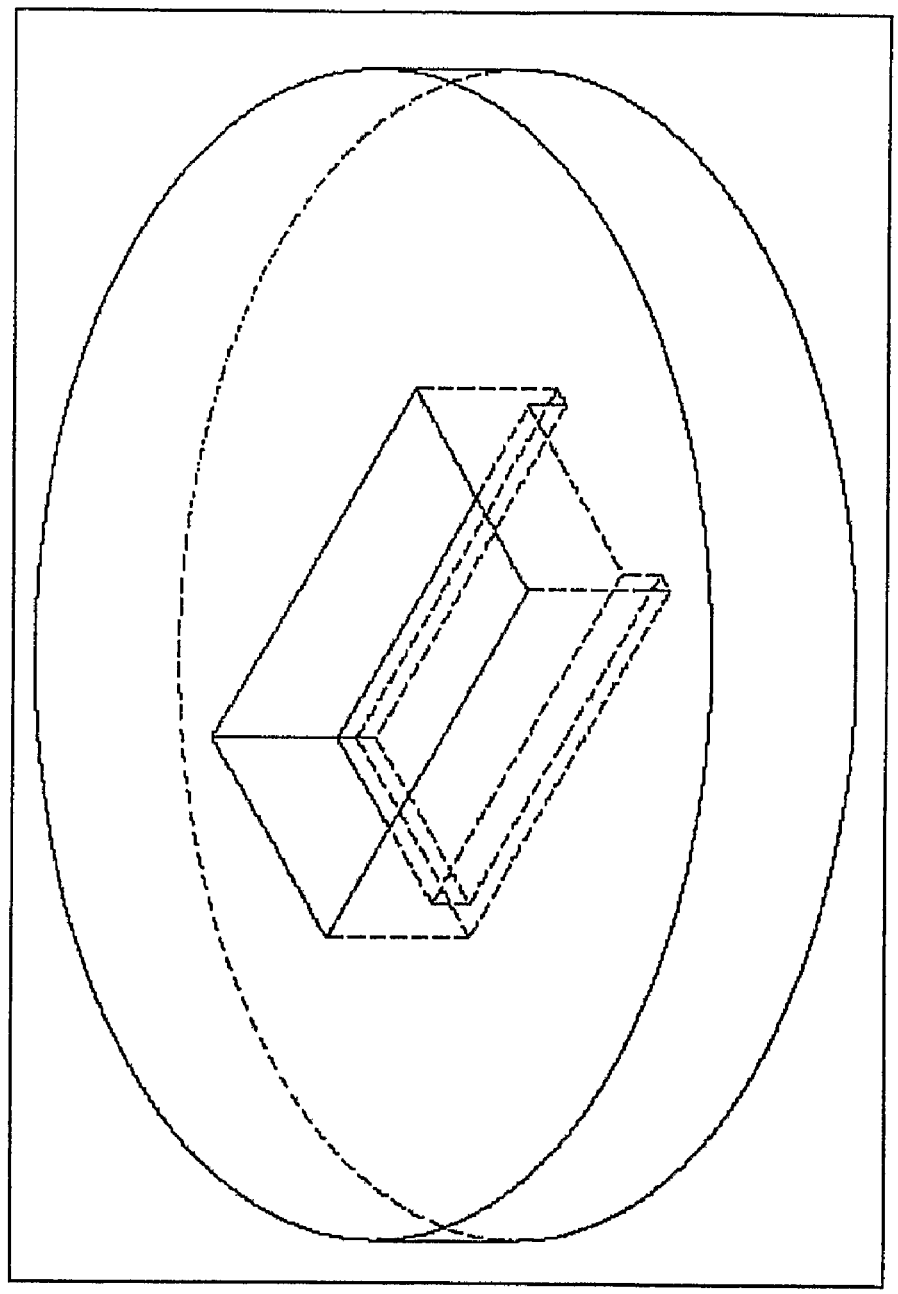
Figures 9B, 9C:
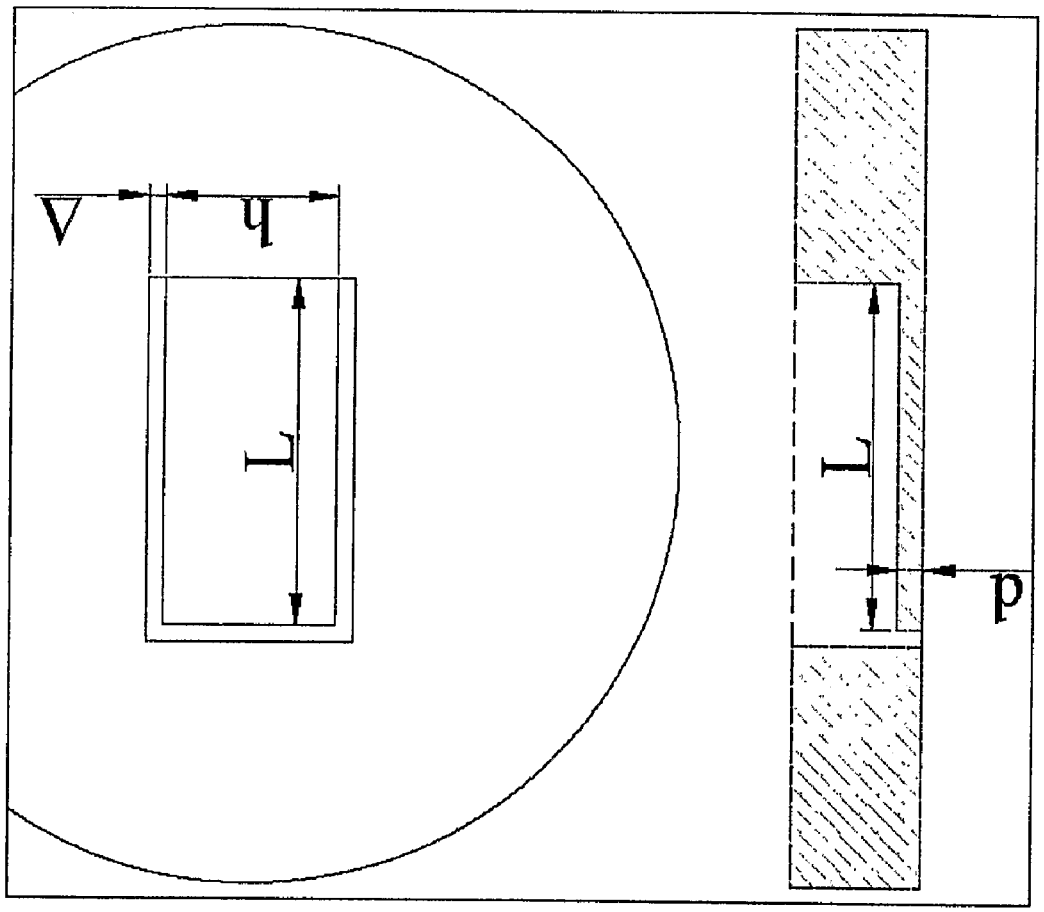
Figure 10:
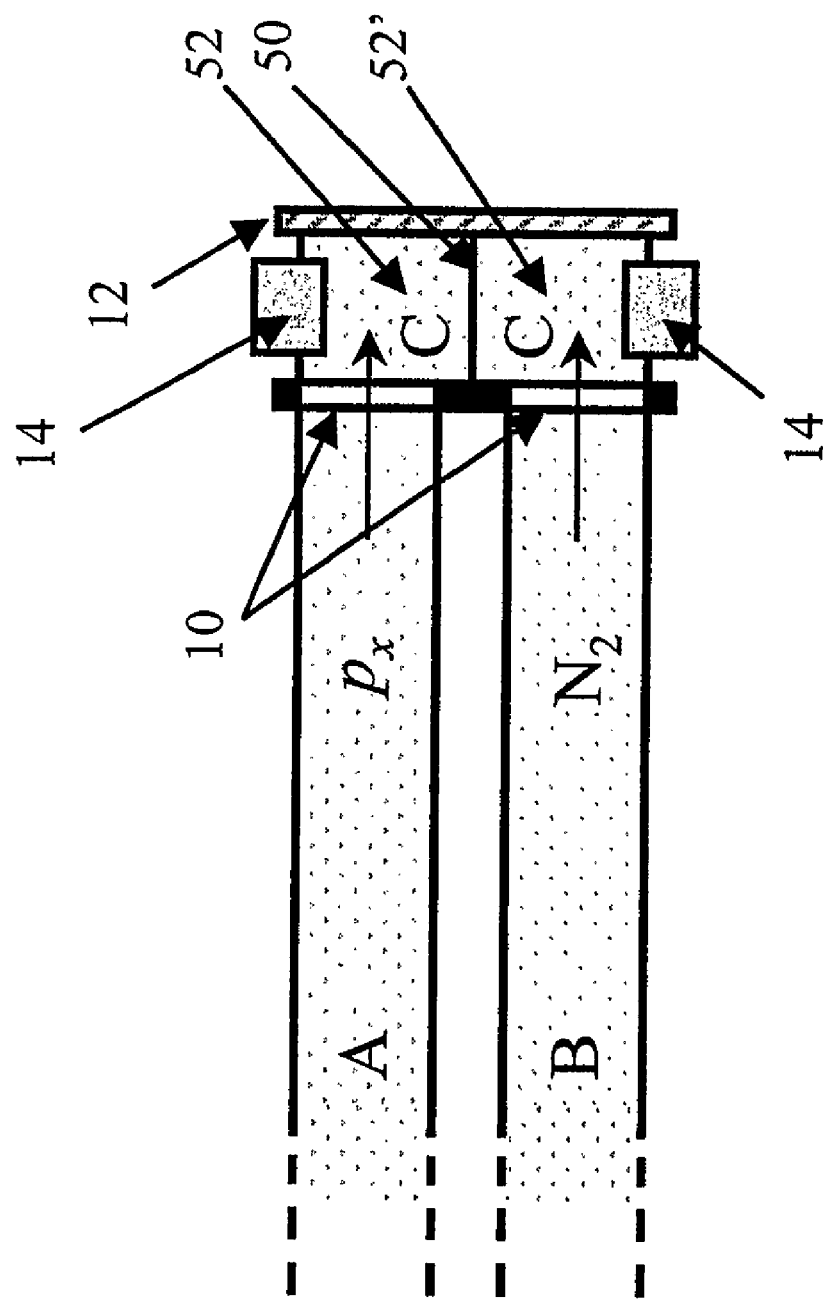
Figure 11:
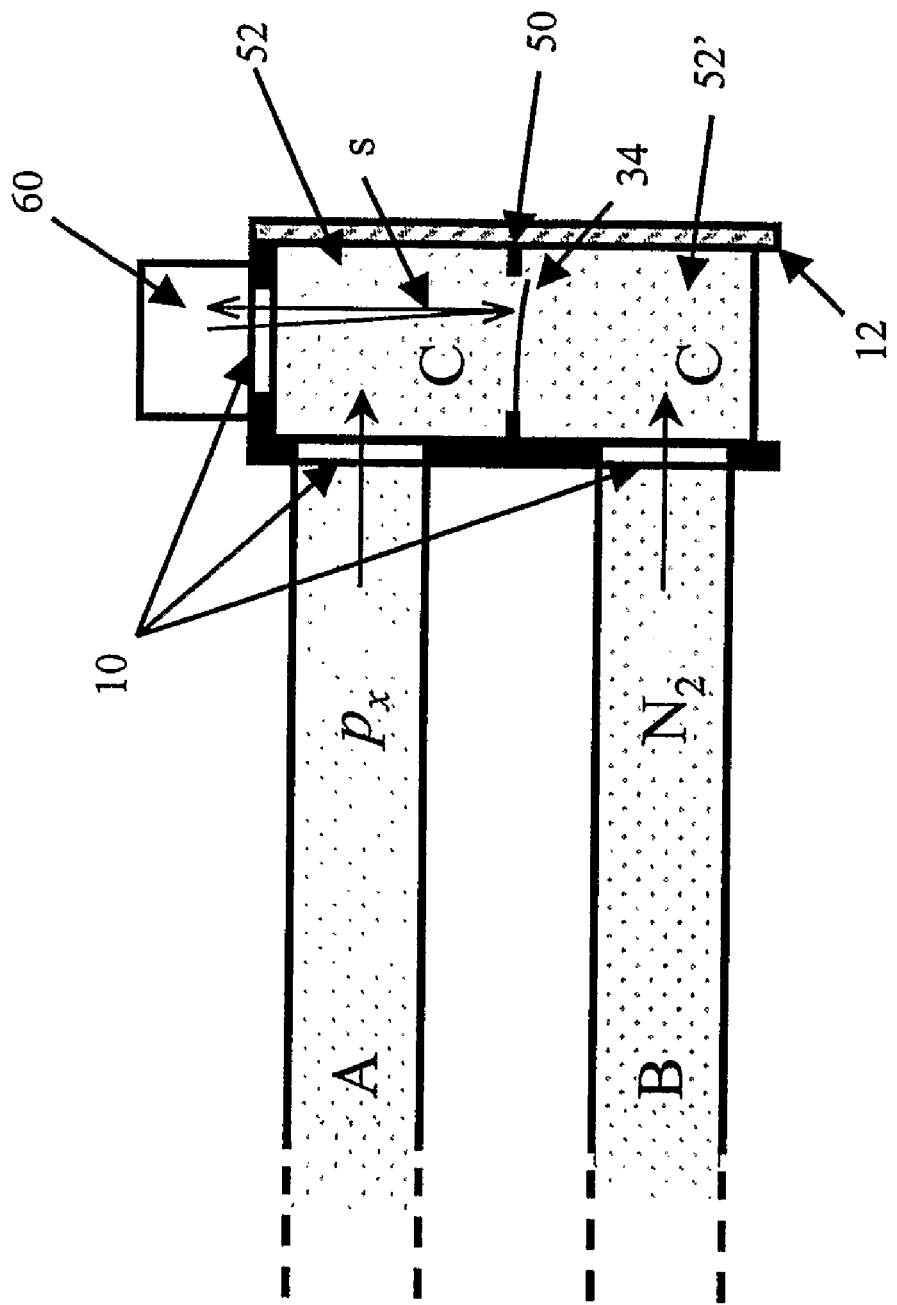
Figure 12:
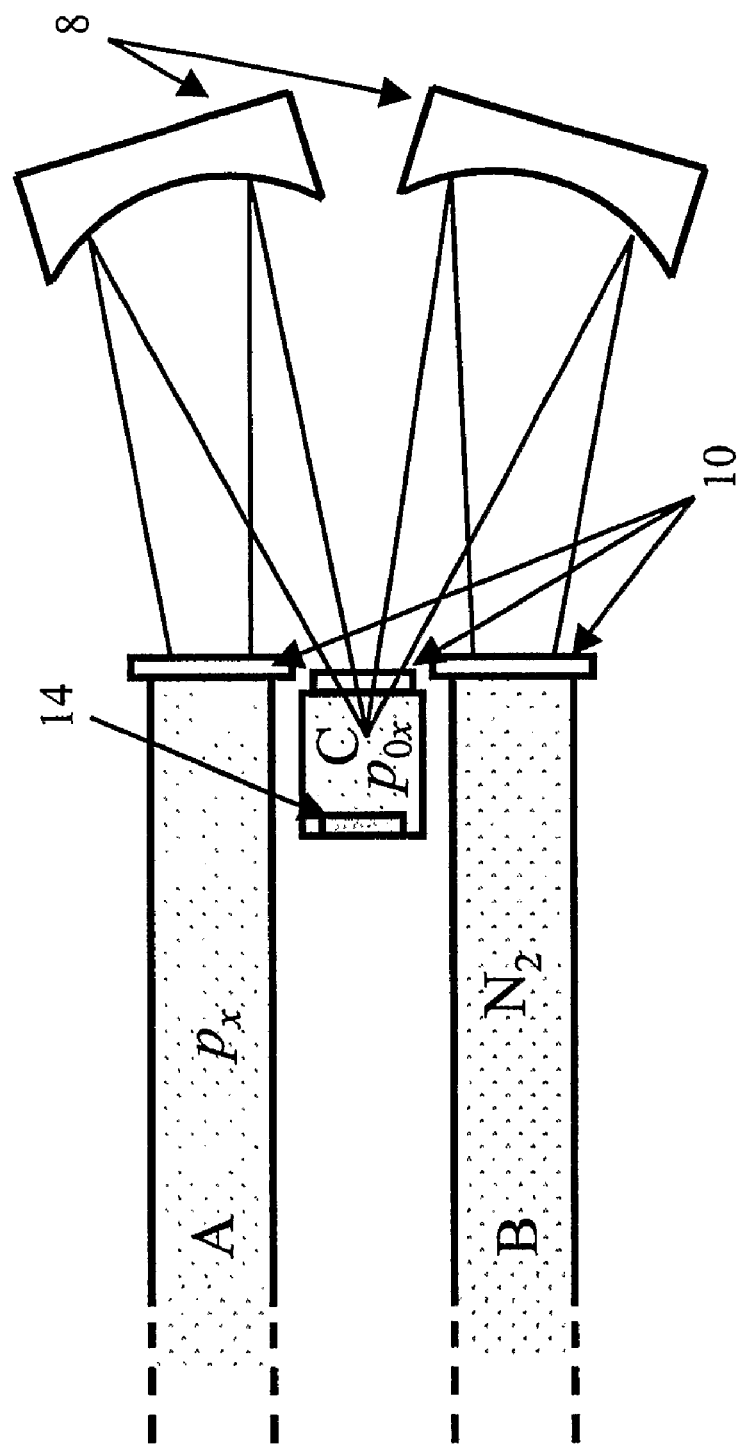
Figure 13:
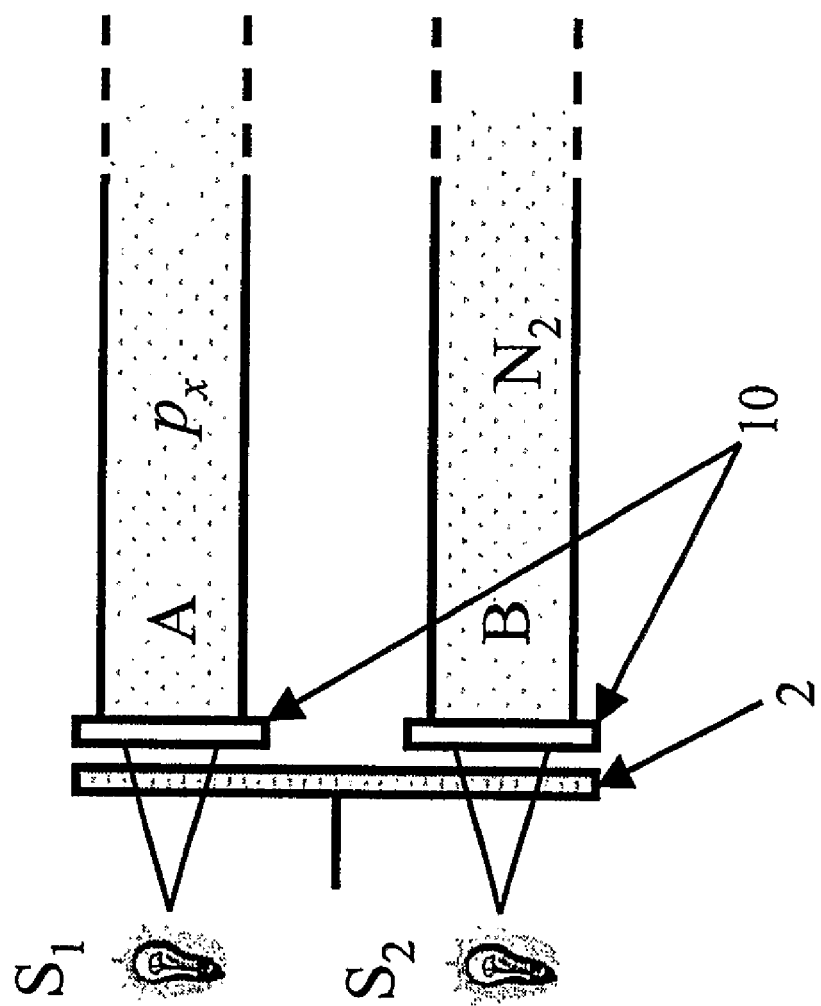
Figure 14:
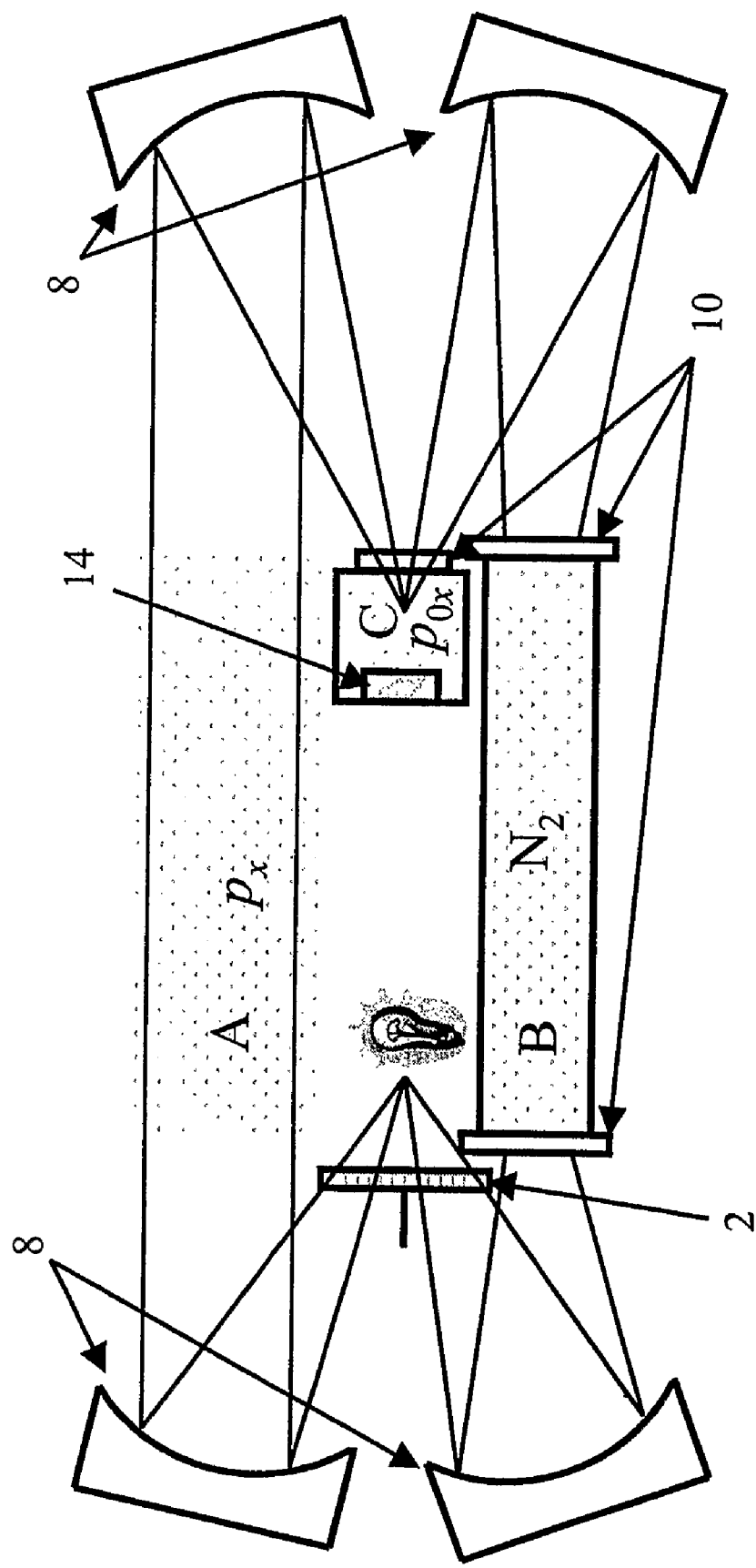
Figure 15:
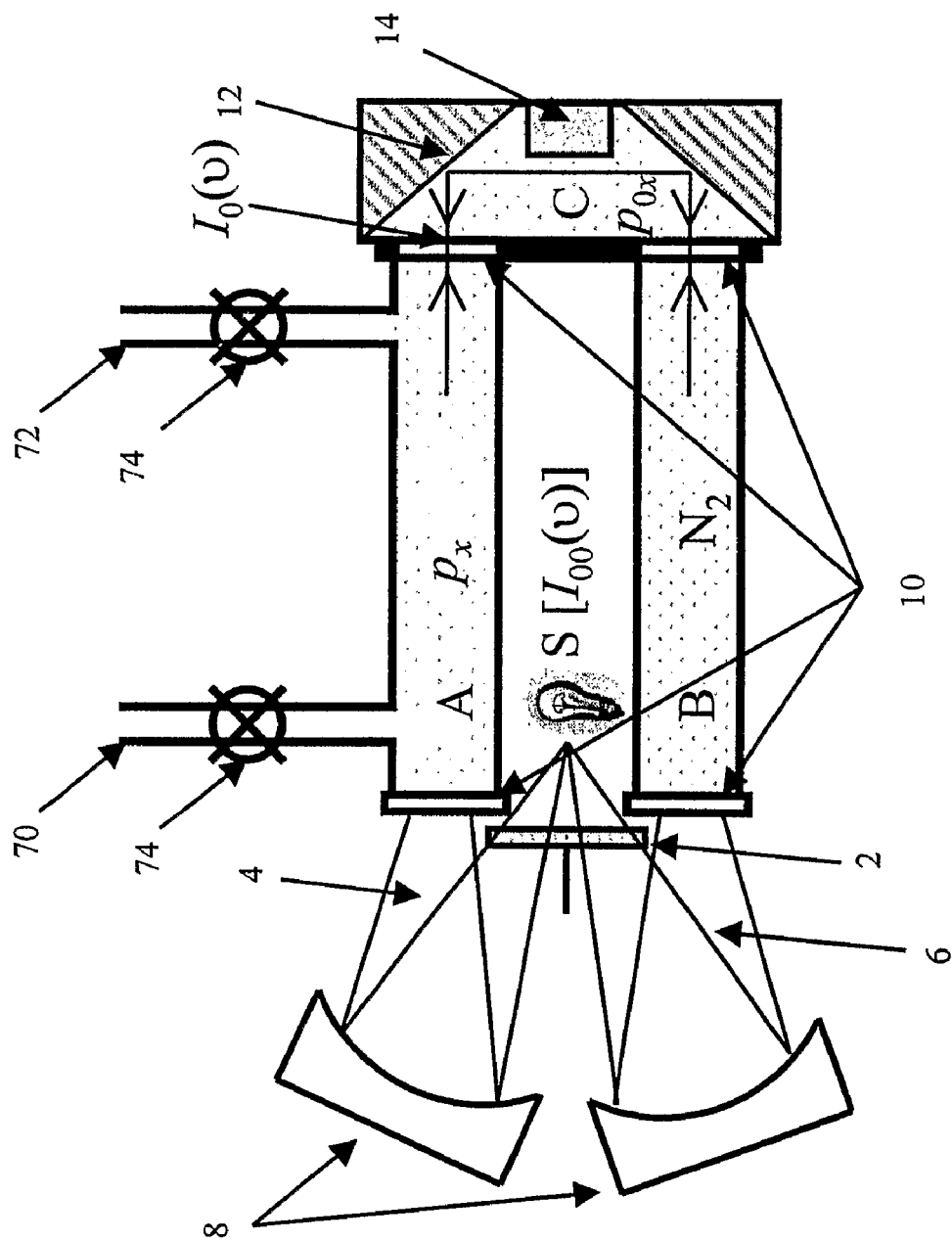

The invention will now be described in more detail with reference to the accompanying drawing, in which FIG. 1 shows schematically a filtering process with an optical filter of the prior art, FIG. 2 shows schematically one embodiment for a measuring method of the present invention, FIG. 3 shows schematically the proportionality of a photoacoustic signal to a partial pressure px of a gas to be measured, FIG. 4 shows schematically one embodiment for a multicomponent analyzer of the present invention, FIG. 5 shows schematically a measuring chamber, which constitutes a Helmholtz resonator by means of a connecting channel, FIG. 6 shows schematically the development of a signal at a changing frequency, the employed measuring chamber comprising a conventional chamber and the measuring chamber being designed as a Helmholtz resonator, FIG. 7 shows schematically one embodiment for a pressure sensor for use in the present invention, FIG. 8 shows schematically one embodiment for a pressure sensor for use in the present invention, FIGS. 9a-9c show schematically one embodiment for a sensor for use in the present invention and arranged to move in response to pressure variations, FIG. 10 shows schematically one embodiment for a measuring chamber of the present invention, FIG. 11 shows schematically one embodiment for a measuring chamber of the present invention, FIG. 12 shows schematically one embodiment for a measuring arrangement of the present invention, FIG. 13 shows schematically one embodiment for a light source arrangement for use in a measuring arrangement of the present invention, FIG. 14 shows schematically one embodiment for a measuring method of the present invention, and FIG. 15 shows schematically one embodiment for a measuring method of the present invention.

DETAILED DESCRIPTION OF THE PREFERRED EMBODIMENTS

FIG. 2 shows schematically a system and a measuring method of the present invention in one embodiment thereof. The system depicted in the figure includes a light source S capable of producing a light beam for use in measuring. A chopper 2 pulses the light beam for a first light beam 4 and a second light beam 6, which are collected by means of spherical mirrors 8 and conducted into a sample chamber A, which functions as a sample space and has a gas mixture to be analysed, containing a gas to be measured at a partial pressure px, and into a reference chamber B functioning as a reference space. The measuring system is arranged such that the first light beam 4 travels through the sample chamber A and thence further into a photoacoustic measuring chamber C. The chambers A and B have their ends closed with windows 10, which transmit the light beams used in measuring, yet at the same time isolate the sample and reference chambers from the ambience together with chamber walls.

Each of the illustrated chambers A and B could have been constructed for example from a metal pipe, which is provided with necessary valves (for example one or several valves) for exhausting and filling the chamber. In addition, the sample chamber A could have been manufactured from a metal pipe, which is provided with a number of holes for providing a free passage for a sample gas in and out of the sample chamber. The measuring chamber C is also provided with means for enabling the filling and eventual draining of the measuring chamber.

As shown in the figure, plane mirrors 12, which deflect the propagation direction of the first and second light beams for an extended path length are arranged in the photoacoustic measuring chamber C. Furthermore, a pressure sensor 14 for detecting pressure variations occurring in the chamber is arranged in the photoacoustic measuring chamber C. Exemplary embodiments for a viable pressure sensor 14 are depicted more precisely in FIGS. 7 and 8.

The exemplary method of the present invention does not use or require a conventional optical filter but, instead, a gas or gas mixture x to be measured and/or detected present at a known pressure p0x in the measuring chamber C makes the photoacoustic measuring chamber function as a detector selective to the gas x. This selective detector is used for a normal transmission measurement of the sample space A. The measuring arrangement of the present invention is comparable with the method described in the publication of Kovalyov and Klebleyev, in which the first chamber functions as a selective filter by means of a known pressure p0x and the second photoacoustic chamber contains a gas mixture to be analysed, from which a partial pressure px is measured. Thus, in the present invention, the chambers have their roles reversed for improved selectivity and sensitivity. This is best explained by the following theory. The photoacoustic measuring chamber C as depicted in FIG. 2 absorbs a power $$I_A = \int_0^\infty I_0(v)(1 - e^{-p_{0x}lE_x(v)})dv, \quad (1)$$

wherein $E_x(v)$ represents an absorption spectrum for a sample x and, v is a wave number. The photoacoustic signal has an amplitude which is proportional to $I_\lambda$. Since $I_0(v)=I_{00}(v)e^{-p_xLE_x(v)}$, in which $I_{00}(v)$ represents the power of a radiation source, the result will be $$I_A = p_{0x}l\int_0^\infty I_{00}(v)E_x(v)dv - p_x p_{0x}Ll\int_0^\infty I_{00}(v)E_x^2(v)dv, \quad (2)$$

wherein L is a distance traveled by the light beam in the sample and l is a distance traveled by the light beam in the measuring chamber.

If $e^{-p_xLE_x(v)} \approx 1-p_xLE_x(v)$ and $1-e^{-p_{0x}lE_x(v)} \approx p_{0x}lE_x(v)$. That is, the equation (2) can be expressed as $$I_\lambda = \text{constants} - p_x\text{constant}' \quad (2')$$

(see FIG. 3). The signal coming through the reference chamber B has an amplitude $$p_{0x}l\int_0^\infty I_{00}(v)E_x(v)dx = \text{constant.}$$

This is obtained from the equation (2), since px=0 as no sample x is present in the chamber, but it may contain some other gas (e.g. $N_2$). If the signal of a radiation passing through the chamber A is subtracted from the signal of a radiation passing through the chamber B, the differential signal will have an amplitude $$I_{B-A} = p_x p_{0x}Ll\int_0^\infty I_{00}(v)E_x^2(v)dv \quad (3)$$

In the system of FIG. 2, the pressure sensor delivers a differential signal if the light beams are in opposite phases. The differential signal has its amplitude measured by means of a phase locked loop (PLL).

The method and system of the present invention provide several benefits over prior art solutions. For example, the measuring method has a very good selectivity as regards the selectivity attainable with spectroscopic methods. If the chamber A contains a sample x at a partial pressure px and a sample y at a partial pressure py and the measuring chamber C still contains only a sample x at a pressure p0x, the radiation passing through the chamber A produces in the measuring chamber C a photoacoustic signal having an amplitude $$I_A = \int_0^\infty I_{00}(v)[1 - L(p_x E_x(v) + p_y E_y(v))]p_{0x}lE_x(v)dv \quad (4)$$

$$= \underbrace{p_{0x}l\int_0^\infty I_{00}(v)E_x(v)dv - p_x p_{0x}Ll\int_0^\infty I_{00}(v)E_x^2(v)dv}_{\text{constant}} -$$

$$p_y p_{0x}Ll\int_0^\infty I_{00}(v)E_x(v)E_y(v)dv$$

Thus, the differential signal has an amplitude $$I_{B-A} = p_x p_{0x}Ll\int_0^\infty I_{00}(v)E_x^2(v)dv + \quad (3')$$
$$p_y p_{0x}Ll\int_0^\infty I_{00}(v)E_x(v)E_y(v)dv$$
$$\approx p_x p_{0x}Ll\int_0^\infty I_{00}(v)E_x^2(v)dv$$

because $$\int_0^\infty I_{00}(v)E_x(v)E_y(v)dv << \int_0^\infty I_{00}(v)E_x^2(v)dv.$$

Generally with different molecules, the absorption lines have different locations and do not overlap at a high resolution (Doppler limit).

In addition, the sample space A can be designed as shown in FIG. 10 in an open structure and even without walls. In this case, the device measures px, which is proportional to the number of those molecules in a sample x, which lie in the path of a beam progressing from a radiation source to the measuring chamber C.

The measuring result is not affected by pressure, temperature, other gases and fluctuations thereof, present in the sample space A.

Another observation is that the measuring method has its sensitivity improved as compared to conventional $$\Delta p_x^{min} \approx \frac{l}{L}\Delta p_x^{min}(\text{convent.}).$$

Thus, a detection threshold $\Delta p_x^{min}$ becomes lower approximately by a factor l/L with respect to a conventional photoacoustic method.

The method of the present invention makes it possible to provide an alarm device, whereby several gases can be detected simultaneously. If the photoacoustic measuring chamber C is filled with a gas mixture, the sum of whose partial pressures is $$\sum_i p_{0i},$$

the equation (3) will result in a signal amplitude $$I_{B-A} = \sum_i p_i p_{0i} Ll \int_0^\infty I_{00}(v) E_i^2(v) dv, \quad (5)$$

wherein $p_i$ are partial pressures of respective gases in the chamber A and $E_i(v)$ is the spectrum of a gas i. The partial pressures $p_{0i}$ can be used for adjusting alarm limits for the discussed gases.

Respectively, it is possible to implement a multi-component analyzer:

a) components are measured in temporal succession. Each gas i is provided with its own chamber $C_i$ containing the gas i at a known partial pressure $p_{0i}$. The chambers $C_i$ are rotated (shifted) to a measuring position in temporal succession $C_1, C_2, C_3, \ldots$. The signals have amplitudes $$I_{B-A}^i = p_i p_{0i} Ll \int_0^\infty I_{00}(v) E_i^2(v) dv, \quad (6)$$

wherein $p_i$ is a partial pressure to be measured of the $i^{st}$ gas component in the chamber A. The chambers $C_i$ can be set in a measuring position either by rotating on a revolving disc ("Revolver") or on a linear plate by means of linear motion.

b) components are measured simultaneously. The chambers $C_i$ are set in succession, such that the beams travel through the measuring chambers (see FIG. 4). The pressure sensors 14 $P_1, P_2, P_3, \ldots$ put out signals for each gas. Another possibility is to place the measuring chambers $C_i$ side by side and to divide the beams passing through the chambers A and B into equal beams, which are optically guided into the measuring chambers $C_i$. The division can be effected by means of beam splitters with no radiation losses.

In order to improve sensitivity even further, the measuring chamber C can be designed as a Helmholtz resonator (see FIG. 5). As depicted in the figure, the measuring chamber C is comprised of two chambers 20 and 22, connected by a passage 24 having a length t and a cross-sectional area A. A measuring chamber as displayed in the figure can be manufactured for example by working the sections of the chamber C in a monolithic piece and by drilling the passage 20 therebetween.

A resonance $$f_0 = \frac{c_0}{2\pi} \sqrt{\frac{2A}{tV_0}}, \quad (7)$$

wherein $c_0$ represents the velocity of sound in a gas, can be utilized by adjusting the frequency of a chopper to $f_0$, according to FIG. 6.

In addition, the back wall can be a mirror for doubling a signal. Furthermore, if a capacitive pressure sensor is replaced by a more sensitive sensor, e.g. a door, which is depicted in more detail in FIGS. 9a-9c as well as in the earlier patent application PCT/FI2003/000684 of the applicant, which also has a distinct resonance, that resonance can be adjusted to $f_0$ as well. We refer to this version as a double resonance sensor. A double resonance can be used for readily increasing a sensor response by multiplier 100. As a whole, the new method is capable of providing a sensor response which is about 1000-fold with respect to a conventional method.

One benefit is that the calibration of a method and system of the present invention is quite straightforward and can be performed automatically. As the chopper is rotating, the chamber A has its window covered to provide a signal amplitude (see equation (2)).

$$I_A = \text{constant} = p_{0x} l \int_0^\infty I_{00}(v) E_x(v) dv, \quad (8)$$

wherein a change is only caused by $p_{0x}$ and $I_{00}(v)$. These quantities appear also in constant', so the calibration keeps the angular coefficient constant (see FIG. 3, Equation (2')). In addition, if $p_{0x}=0$, the signal is always 0. Each component, which is to be measured, needs just one calibration value $I_\lambda$ (Equation (8)). For comparison, it can be noted in this context, that typical sensors of the prior art require spectra for all those substances present in a gas to be examined, although there is no desire even to measure their concentrations.

The method is also functional by filling the chamber A to pressure $p_{0x}$ and having in the measuring chamber C a gas to be measured, e.g. px and py.

The accuracy of prior known gas measuring systems, such as the measuring systems presented in the early part of this application, can also be improved by replacing the prior art capacitive measurement of a door (or diaphragm) motion by an optical measuring system of the present invention. Optical measuring interferes very little with the movement of a door (or a diaphragm). According to the present invention, the motion can be measured either by means of the angle of a door (or a diaphragm) or the translatory displacement of some point at a door (or a diaphragm).

FIGS. 7 and 8 illustrate schematically and by way of an example some embodiments for a pressure sensor, which are viable in an assembly and method of the present invention.

FIG. 7 shows a measuring arrangement based on angular measurement, which makes use of an optical indicator provided by a laser 30, the detector comprising a double sensor 32. In addition to a door 34, which functions as a sensor, the measuring assembly comprises the laser 30 functioning as a light source, an optical lens (not shown in the figure) for focusing a light beam, and the double sensor 32 for receiving and measuring a light beam v reflected from the door 34 to the double sensor 32. Hence, the double sensor comprises a first detector and a second detector. The assembly is implemented in such a way that the light beam v has its focal point at the double sensor. FIG. 7 illustrates a door which moves in response to a pressure variation applied thereto. The door design is depicted in more detail hereinbelow with reference to FIGS. 9a-9c. In some embodiments, the door can also be replaced by a microphone, a thin Mylar or metal diaphragm, which moves in response to pressure variations applied thereto. The advantage of a door over a more conventional diaphragm is the door's higher sensitivity to pressure fluctuations.

The angular measurement shown in FIG. 7 has its angular shift $\Delta\alpha$ converted to a translatory motion $\Delta y=\alpha 2\Delta\alpha$, which is measured with the double sensor 32. The angle $\Delta\alpha$ is an average angular shift within a section of the door illuminated by the laser beam.

Advantages offered by an optical indicator as depicted in FIG. 7 include e.g. its simple design, non-interference with the door or diaphragm movement, and the fact that the double sensor suppresses the photon noise of laser light. Preferably, the size of a laser light spot on the door is large.

The movement of a door or diaphragm shown in FIG. 7 can also be measured as translatory measurement. In addition to a door, such an assembly would involve, the same way as the assembly shown in FIG. 7, a laser to function as a light source, a double sensor, and a first optical lens. However, a translatory measuring assembly would be different to what is shown in FIG. 7 in the sense that said first optical lens would be used for aligning the focus of a light beam onto the face of a door presently in a rest or immobile state. The assembly would further comprise a second optical lens for focusing a light beam reflecting from the door onto the double sensor. The light source, the optical lenses, and the double sensor would be arranged in translatory measurement in such a way that, when the door/diaphragm is at rest, there is a 90-degree angle between light beams arriving at and reflecting from the door. An advantage offered by translatory measurement is e.g. that the laser beam is in focus on the face of a door and the door may be of a poor optical quality.

According to one embodiment of the present invention, the movement of a door (or a diaphragm) can be measured optically also by means of an interferometer. FIG. 8 depicts one measuring arrangement applicable to the present invention for measuring the movement of a door (or a diaphragm) with a so-called Michelson interferometer. As shown in the figure, the arrangement comprises, in addition to a door 34 itself, a laser 30 to function as a light source, an optical lens (not shown in the figure) for focusing a laser beam, a beam splitter 36 i.e. a semi-transparent mirror or semireflector for dividing the laser beam for the door 34 and a reference mirror 38, a reference mirror 38 and a triple sensor 40 for receiving laser beams coming from the beam splitter 36. In the arrangement, the laser beam is approximately in focus both on the door and on the reference mirror. The reference mirror 38 is adjusted such that ¾ of an interference line perpendicular to the plane of paper develops on the triple sensor 4o composed of three sensors. When x changes as the door moves, the interference line moves laterally across the detectors. The line travels across one line space as x changes by $\lambda/2$, in which $\lambda$ represents a wavelength for the laser 30.

If the door movement is small $<\lambda/4$, a triple sensor in the above-described measuring arrangement can be replaced by a double sensor similar to the one used in the optical indicator.

Benefits of interferometric measuring as shown in FIG. 8 include e.g.: response is highly linear, even if the movement of a door (or a diaphragm) covers several wavelengths. Absolute accuracy is high because the shape of an interference signal is precisely consistent with the $\frac{1}{2}(1+\cos(2\pi z/D))$ shape. In addition, the laser can be focused on the measuring point of a door almost like a dot, nor does diffraction affect the result. Neither does a variation of the laser power $I_{00}$ affect the value of a measuring result.

When comparing an optical indicator as shown in FIG. 7 and an interferometer as shown in FIG. 8 with each other, it can be concluded that both measuring arrangements provide a substantial improvement regarding the accuracy and sensitivity of measuring. Interferometric measuring is even somewhat more accurate than an optical indicator, but at the same time the measuring arrangement is slightly more complicated. Thus, the necessary sensitivity must be considered and the employed measuring method chosen according to a particular application and case.

A pressure sensor as shown in FIGS. 7 and 8 can be coupled for example with measuring arrangements depicted in FIGS. 2, 4, 5, 10, 12, 14, and 15 by providing the measuring chamber C with an aperture, to which the pressure sensor is tightly fitted. When, after the coupling of a pressure sensor, the measuring chamber C is filled with a gas, the pressure sensor's interior will be filled as well. When the gas present in the measuring chamber C is subjected to pressure fluctuations during a measuring procedure, the door (or the diaphragm) moves and the movement of the door (or the diaphragm) can be measured with optical measuring arrangements shown in FIGS. 7 and 8.

In some embodiments, a contact-free measurement of the door (or diaphragm) movement can be effected for example capacitively, instead of optical measuring, such as the optical measurements shown in FIGS. 7 and 8. However, optical measuring offers a benefit of better sensitivity as the door or diaphragm is not subjected thereby to forces hindering or impeding its movement.

FIGS. 9a-9c depict schematically and by way of an example one silicon-made door according to the present invention, which functions as a pressure sensor. The pressure sensor comprises a panel-like frame element to function as a door frame or jamb, and a door separated by a slot from the panel-like element. L represents a lateral dimension of the door, h is its height, d is its diameter, and $\Delta$ is a width of the slot.

When using a door sensor according to the embodiment shown in FIGS. 9a-9c, it is necessary to make a gap between the door and the wall preferably as narrow as possible. The measuring chamber leaks through the gap, which results in the sensor having a lower threshold frequency $f_{cut}$, which is determined by the area of a door gap, $$f_{cut} \propto v_0 \frac{a}{V_0}.$$

On the other hand, it is preferred that between chamber of the pressure sensor and the measuring chamber C be provided a small hole, which equalizes slow pressure variations between the chambers and which hole can thus be designed as a previously mentioned gap between the door and the door frame. The optimization of a door design has been described in more detail in the above-cited earlier patent application PCT/FI2003/000684 of the applicant, the contents and specifications of which are incorporated herein as part of the specification of this application.

FIG. 10 shows schematically one embodiment for a measuring chamber of the present invention, which is feasible in a system and method of the present invention. The measuring chamber depicted in FIG. 10 is different to that shown e.g. in FIG. 2 in the sense that the measuring chamber C is composed of two chambers 52 and 52' separated from each other by a wall 50. The chambers 50 and 50' are practically identical to each other, i.e. matching each other in terms of size and shape. In other words, there is a separate chamber for each of the first beam and the second beam. A pressure sensor 14, for example a pressure sensor like the one shown in FIGS. 7 and 8, has been arranged in both chambers. Gas to be measured the same way as the chamber C shown in FIG. 2 has been arranged in each chamber 52 and 52'. As shown in FIG. 10, the chambers 52 and 52' comprise a window in the forward part thereof for admitting the first and second beams into the chambers 52 and 52'. It is also possible to arrange two separate windows for in the forward part admitting the beams into the chambers. As shown in the figure, the chambers 52 and 52' have the back wall thereof comprising a mirror for retroreflecting the beams entered in the chambers to thereby extend the distance covered by the beams within the chambers.

FIG. 11 shows schematically yet another embodiment for a measuring chamber of the present invention, which is feasible in a system and method of the present invention. In the measuring chamber of FIG. 11, the measuring chamber is divided by a wall 50 into two chambers 52 and 52', the same way as the measuring chamber shown in FIG. 10. Thus, the chambers 52 and 52' are mutually identical, i.e. they are equal in terms of volume and preferably in terms of shape. The measuring chamber shown in FIG. 11 is different to that shown in FIG. 10 in terms of the monitoring and/or measuring of pressure variations occurring in the chamber. As shown in FIG. 11, the wall 50 is provided with a hole for connecting the chambers 52 and 52' to each other, whereby the measuring chamber can be perceived as a single chamber comprising two sub-chambers. The hole in the wall 50 is provided with a door 34, for example similar to the one shown in FIG. 7, 8 or 9a-9c.

Prior to measuring, gas or gas mixture to be measured/detected, typically at a known pressure $p_{0x}$ is arranged in the measuring chamber, the gas or gas mixture being present in each chamber 52 and 52' at the same pressure. Thus, in a normal situation, i.e. when a gas is not measured/detected or when no gas or gas mixture to be detected/measured is present in the sample space, there is no pressure difference between the chambers 52 and 52' and the door is stationary. The door 34 moves as pressure variations occur in the measuring chamber, i.e. in the chamber 52 and/or 52', for example in such a way that the chambers 52 and 52' develop a pressure difference therebetween in response to light beams conducted into the chambers.

According to what is shown in FIG. 11, in order to detect a movement of the door 34, an optical measuring arrangement 60 capable of detecting or measuring a movement of the door 34 is arranged in the measuring chamber, i.e. in communication with the chamber 50 as shown in the figure. As a viable optical measuring arrangement it is possible to use for example arrangements depicted and described in reference to FIGS. 7 and 8. Thus, the measuring chamber 52 is provided with an aperture closed by a window 10, through which a laser beam s for use in measuring can be conducted into and out of the chamber.

FIG. 12 shows one embodiment, wherein the beams that have passed through a sample space (A) and a reference space (B) are guided or deflected into a common measuring chamber (C) by means of spherical mirrors 8.

FIG. 13 shows schematically one embodiment for producing beams viable in a measuring arrangement. The solution of FIG. 13 comprises two separate light sources $S_1$ and $S_2$. The viable light sources $S_1$ and $S_2$ are provided for example by a laser. If the light sources are modulated alternately, a chopper can be omitted.

FIG. 14 shows schematically one exemplary embodiment for implementing a system and method of the present invention. As shown in FIG. 14, a sample space A is completely open to its ambience for providing for a gas or gas mixture to be measured/detected a totally free passage into and out of the sample space without having to separately fill the sample space for a measuring procedure. An open sample space is particularly viable in various alarm and surveillance applications. Exemplary applications regarding the uses of an open sample space include, for example, permanently installed or personal, mobile alarm devices for detecting gases or gas compounds. In addition, an open sample space can be exploited in various industrial production processes.

FIG. 15 shows schematically one embodiment for the arrangement of FIG. 2. As shown in FIG. 15, to the sample space A extends a supply pipe 70, which is connected to the process duct of an industrial process, such as a gas line or a pipe containing gases. Along the supply pipe 70 gas or gas mixture to be analysed can be delivered into the sample space for detecting a desired gas or gas mixture and/or for measuring its concentration. To the sample space A is also connected a return pipe 72, along which gas delivered into the sample space A can be discharged from the sample space. The passage of the gas to be analysed into a sample space can be provided for example by means of the pressure or movement of a gas acting in the actual process duct or pipe, the gas migrating along the supply pipe into the sample space and further out of the sample space along the return pipe. The supply pipe 70 and the return pipe 72 are further provided with valves 74 for regulating the flow rate of a gas/gas mixture into and/or out of the sample space. In some applications, either the supply pipe or the return pipe can be fitted with a pump for enhancing the flow of a gas/gas mixture.

A system and method of the present invention can be used in a multitude of various applications and purposes. Notable applications in this respect include industrial measurements, such as in pharmaceutical, chemical, process, and forest industries, process controls and managements. In addition, the systems and measuring methods according to the present invention can be used, for example, in measuring and controlling discharges from power facilities and combustion processes, as well as in the management of such processes.

A system of the present invention can be additionally used as a measuring and/or monitoring device in also other process applications and in process control and regulating systems. Examples of such applications include control or regulation measurements in the manufacturing processes of semiconductor industry, such as for example measurements for the concentrations and type of various gases, various controls for production and working processes of stocks in paper and board industries, for example measurements for the amount of chemicals in papermaking, either from a finished paper web, from the wet end of a paper machine or from some other process, prior to applying the chemicals to the paper web. Further examples about appropriate process industrial applications include various processes in pharmaceutical, chemical, and petrochemical industries, and various operations therein.

A system and method of the present invention can be used alone or as an integrated part of some other measuring or monitoring system. It is further possible that a system of the present invention be accompanied with additional systems or devices for vaporizing the examined substance, in which case a measurement of the present invention can be performed from vaporized gas. It is additionally possible that a substance under examination be subjected to radiation at a desired wavelength range, the radiation absorbing into the substance to facilitate a measuring procedure. As pointed out above, the substance being examined may thus be either in the form of a gas, a liquid or in a solid state. Hence, a system and method of the present invention can be used, for example, in measuring or monitoring the properties or quality of conveyor-carried pieces, in measuring the properties of a paper web in paper industry, as well as in measuring living creatures.

A system of the present invention can also be used in measuring liquids, such that the measurement is performed through a liquid, either a liquid to be measured/detected or a gas desired to be measured/detected from the liquid being arranged in the measuring chamber.

A system of the present invention can also be linked to an on-line system. If a partially or completely open sample space is used in accordance with the invention in an on-line system, the measurement can be effected in a very simple and reliable manner as a separate sample-space filling system and mechanism is not absolutely necessary.

Moreover, systems and methods of the present invention can be used in various portable and fixed gas analyzers, such as respiratory air analyzers, as well as in various alarms, such as carbon monoxide or flue gas alarm devices.

Still further, a system and method of the present invention can be used alone or as one of the components in alarms and devices based on measuring respiratory air, which can be used for example in sports equipment and sports research. A notable example of such sports equipment comprises test equipment for use in sports training, as well as for example devices, such as diving computers, for use in diving and based at least partially on analysing or measuring respiratory air.

As described above, a system and method of the present invention can be used in a wide range of applications. The system and method can be used for example in food industry in general quality control and monitoring measurements, as well as especially in process control, in sensory automation of analysis, in microbiology, in controlling the use of banana ripening ethylene, as well as in supervision of food storage. In addition, the system can be used in measurements for air quality, such as emissions, in various applications of environmental and building technology, as well as in automotive and energy industries for measuring e.g. industrial emissions, in building automation applications, as well as in implementations regarding seminar room alarms.

The present invention is also applicable for implementing a multitude of measuring equipment and alarms required/employed in security industry, e.g. for detecting fires (for example a smoke and/or carbon monoxide alarm), toxic discharges, poison and combat gases, as well as other agents harmful or hazardous to humans or animals. Additionally, technology according to the present invention can be applied for designing alcometers and other measuring/detection equipment needed in the investigation of a possible crime (for example, fire starting analyses, crime scene investigation).

A system and method of the present invention can be used for designing not only a respiratory air meter as described above but also actual diagnostics equipment for respiratory air. Examples of such applications include measuring equipment for measuring the gases of respiratory air, noninvasive Hb measuring, noninvasive glucose measuring, noninvasive CO2 or O2 measuring, noninvasive blood gas analysis, as well as analyses and measurements for bacterial strain in abdomen.

It is further possible to design measuring equipment, which can be used in building technology for structural mould measurements and in materials technology for example in the identification of materials and in research relating to the behaviour and gas discharges of materials.

The invention is by no means intended to be limited to the embodiments described in the foregoing specification, but it can be varied within the inventive concept disclosed in the claims and specification. Modifying various forward and rearward sections makes it possible to construct a wide variety of analyzers and measuring systems. In addition, the above-described measuring chambers of the present invention can be used also in other measuring systems for detecting a photoacoustic signal. Furthermore, a measuring chamber of the present invention can also be accompanied by radiation sources, reference chambers, and sample spaces other than those described above. It is natural for a person skilled in the art that a measuring chamber of the present invention can be integrated and used for major benefits also in measuring systems not including a reference chamber.

The invention claimed is:

1. A system for detecting one or more gases or gas mixtures and/or for measuring the concentration of one or more gases or gas mixtures, said system comprising at least:
   at least a first light source,
   a sample space where gas to be detected and/or measured can be arranged,
   a reference space isolated from the sample space and containing no gas to be detected and/or measured,
   a measuring chamber, which has a volume V, and to a wall of which at least one aperture is arranged, said at least one aperture being provided with a window for admitting modulated and/or pulsed infrared radiation and/or light into the measuring chamber, and to which measuring chamber gas or gas mixture to be detected and/or measured is arranged,
   means for conducting a first light beam from the at least first light source into the sample space and further into the measuring chamber,
   means for conducting a second light beam, in isolation from the sample space, from the first light source or from a second light source into the reference space and further into the measuring chamber, and
   means for pulsing the first and second light beams, wherein the measuring chamber comprises two chambers in communication with each other by way of an aperture, a first being supplied with said first light beam and a second being supplied with said second light beam, and that the aperture has been arranged to a door arranged to move in response to a pressure difference between the first and second measuring chambers, and that the measuring chamber includes means for measuring the door movement without contact.

2. A system as set forth in claim 1, wherein the system comprises means for subtracting a photoacoustic signal produced by the first light beam from a photoacoustic signal produced by the second light beam.

3. A system as set forth in claim 1, wherein the system comprises a phase locked loop for measuring the amplitude of a photoacoustic signal.

4. A system for detecting one or more gases or gas mixtures and/or for measuring the concentration of one or more gases or gas mixtures, said system comprising at least:
   at least a first light source,
   a sample space where gas to be detected and/or measured can be arranged,
   a reference space isolated from the sample space and containing no gas to be detected and/or measured,
   at least one measuring chamber, which has a volume V, and to a wall of which at least one aperture has been arranged, said at least one aperture being provided with a window for admitting modulated and/or pulsed infrared radiation and/or light into the at least one measuring chamber, and to which measuring chamber gas or gas mixture to be detected and/or measured has been arranged,
   means for conducting a first light beam from the first light source into the sample space and further into the at least one measuring chamber,
   means for conducting a second light beam, in isolation from the sample space, from the first light source or from a second light source into the reference space and further into the at least one measuring chamber or a second measuring chamber complementary to the first one, and
   means for pulsing the first and second light beams, wherein the at least one measuring chamber, and the second measuring chamber, comprises means for detecting pressure variations produced in the at least one measuring chamber by absorbed infrared radiation and/or light, said means comprising at least:

an aperture provided in a wall of the at least one measuring chamber, which is provided with a door adapted to move in response to a gas pressure variation, and means for measuring the door movement without contact.

5. A system for detecting one or more gases or gas mixtures and/or for measuring the concentration of one or more gases or gas mixtures, said system comprising at least:

at least a first light source, a sample space where gas to be detected and/or measured can be arranged, a reference space isolated from the sample space and containing no gas to be detected and/or measured, a measuring chamber, which has a volume V and has its wall provided with at least one aperture, to which at least one aperture a window is arranged for admitting modulated and/or pulsed infrared radiation and/or light into the measuring chamber, and to which measuring chamber gas or gas mixture to be detected and/or measured has been arranged, means for conducting a first light beam from the first light source into the sample space and further into the measuring chamber, means for conducting a second light beam, in isolation from the sample space, from the first light source or from a second light source into the reference space and further into the measuring chamber, and means for pulsing the first and second light beams, wherein the measuring chamber comprises two chambers in communication with each other by way of an aperture, a first being supplied with said first light beam and a second being supplied with said second light beam, and that a sensor arranged to move in response to a gas pressure variation occurring in the first and/or second chamber of the measuring chamber has been arranged in the aperture, and means for measuring the sensor movement optically.

6. A method for detecting one or more gases or gas mixtures or for measuring the concentration of one or more gases or gas mixtures, said method comprising at least the following steps of:

conducting a first light beam into a sample space where gas to be detected and/or a gas mixture to be measured has been arranged for measuring a desired component x thereof for its partial pressure px, and further into a measuring chamber isolated from the sample space, to which measuring chamber gas, which is to be detected and/or measured and which is at a known pressure $p_{0x}$ has been arranged, and said measuring chamber comprising two chambers in communication with each other by way of an aperture, a first one being supplied with said first light beam, and to which aperture between the chambers a door arranged to move in response to a pressure difference between the first and second measuring chambers has been arranged, conducting a second light beam into a reference space isolated from the sample space and further into a measuring chamber isolated from the reference space, such that the second light beam, at least before the measuring chamber, is always isolated from the sample space and arrives in a section of the measuring chamber other than the one receiving the first light beam, pulsing the first and second light beams, such that a photoacoustic signal is produced thereby for a photoacoustic pressure sensor arranged in the measuring chamber, and detecting the photoacoustic signal by measuring said door movement without contact, said signal being used for detecting the gas x and/or for measuring the concentration or the partial pressure px of a gas from the gas mixture.

7. A method as set forth in claim 6, wherein the method is applied for a simultaneous detection of several gases, whereby the mixture of gases subjected to detection is arranged to the measuring chamber and, by adjusting known partial pressures of the gases, a detection threshold is determined for one or more gases.

8. A method as set forth in claim 6, wherein the method is applied for a simultaneous detection of several gases, the various gases being measured in temporal sequence by arranging for each gas to be measured a measuring chamber, which is isolated from other chambers and comprises a photoacoustic pressure sensor and where gas to be measured is arranged, and wherein the measuring chambers are arranged to receive the first and second light beams for effecting a measurement in temporal sequence.

9. A method as set forth in claim 6, wherein the method is applied for a simultaneous detection of several gases, the various gases being measured in temporal sequence by arranging for each gas to be measured a measuring chamber, which is isolated from other chambers and comprises a photoacoustic pressure sensor, and to which gas to be measured is arranged, and by placing the measuring chambers in such a configuration that the first light beam and the second light beam travel through the measuring chambers.

10. A method for detecting one or more gases or gas mixtures or for measuring the concentration of one or more gases or gas mixtures, said method comprising at least the following steps of:

conducting a first light beam into a sample space where gas to be detected and/or a gas mixture to be measured is arranged for measuring a desired component x thereof for its partial pressure px, and further into a measuring chamber isolated from the sample space, to which measuring chamber gas, which is to be detected and/or measured and which is at a known pressure $p_{0x}$ is arranged, and said measuring chamber comprising two chambers in communication with each other by way of an aperture, a first one being supplied with said first light beam, and to which aperture between the chambers a sensor arranged to move in response to a pressure difference between the first and second measuring chambers is arranged, conducting a second light beam into a reference space isolated from the sample space and further into a measuring chamber isolated from the reference space, such that the second light beam, at least before the measuring chamber, is always isolated from the sample space and arrives in a section of the measuring chamber other than the one receiving the first light beam, pulsing the first and second light beams, such that a photoacoustic signal is produced thereby for a photoacoustic pressure sensor arranged in the measuring chamber, and detecting the photoacoustic signal by measuring said sensor movement optically, said signal being used for detecting the gas x and/or for measuring the concentration or the partial pressure px of a gas from the gas mixture.

11. A method for detecting one or more gases or gas mixtures or for measuring the concentration of one or more gases or gas mixtures, said method comprising at least the following steps of:

conducting a first light beam into a sample space where gas to be detected and/or a gas mixture to be measured is arranged for measuring a desired component x thereof for its partial pressure px, and further into a measuring chamber isolated from the sample space, to which measuring chamber gas, which is to be detected and/or measured and which is at a known pressure $p_{0x}$ is arranged, and which measuring chamber has a volume V, and to a wall of which measuring chamber a window for admitting a first light beam into the measuring chamber is arranged, and said measuring chamber comprising means for detecting pressure variations produced in the measuring chamber by absorbed infrared radiation and/or light, said means comprising at least:

an aperture arranged in a wall of the measuring chamber, in connection to which aperture a door arranged to move in response to a gas pressure variation is arranged, and means for measuring the door movement without contact, conducting a second light beam into a reference space isolated from the sample space and further into a measuring chamber isolated from the reference space, such that the second light beam, at least before the measuring chamber, is always isolated from the sample space and arrives in the measuring chamber through said window or a separate second window arranged to the measuring chamber, pulsing the first and second light beams, such that a photoacoustic signal is produced thereby for a photoacoustic pressure sensor arranged in the measuring chamber, and detecting the photoacoustic signal by measuring with the above-identified means, and using the detected photoacoustic signal for detecting the gas x and/or for measuring the concentration or the partial pressure px of a gas from the gas mixture.

12. A measuring chamber for detecting or measuring a photoacoustic signal, wherein the measuring chamber comprises two chambers in communication with each other by way of an aperture, the first being suppliable with a first light beam and the second being suppliable with a second light beam, and that a door arranged to move in response to a pressure difference between the first and second measuring chambers is arranged in the aperture, and that the measuring chamber comprises means for measuring the door movement without contact or the measuring chamber has means connectible therewith for measuring the door without contact.

13. A measuring chamber for detecting or measuring a photoacoustic signal, wherein the measuring chamber comprises means for detecting pressure variations produced in the measuring chamber by absorbing light in the chamber, said means comprising at least an aperture arranged in a wall of the measuring chamber, in connection with which aperture a door arranged to move in response to a gas pressure variation is arranged, and means for measuring the door movement without contact.

14. A measuring chamber for detecting or measuring a photoacoustic signal, wherein the measuring chamber comprises two chambers in communication with each other by way of an aperture, a first being suppliable with a first light beam and a second being suppliable with a second light beam, and that a sensor arranged to move in response to a gas pressure variation occurring in the first and/or second chamber of the measuring chamber is arranged in the aperture, and means for measuring the sensor movement optically.

* * * * *